(12) United States Patent
Houhou et al.

(10) Patent No.: US 9,487,582 B2
(45) Date of Patent: Nov. 8, 2016

(54) METHODS FOR TREATING PANCREATIC CANCER

(75) Inventors: Leïla Houhou, Montpellier (FR); Dominique Joubert, Sète (FR); Frédéric Hollande, Les Matelles (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIQUE (CNRS), Paris (FR); LES LABORATORIES SERVIER, Suresnes (FR)

( * ) Notice: Subject to any disclaimer, the term of this patent is extended or adjusted under 35 U.S.C. 154(b) by 714 days.

(21) Appl. No.: 12/984,522

(22) Filed: Jan. 4, 2011

(65) Prior Publication Data

US 2011/0171213 A1 Jul. 14, 2011

Related U.S. Application Data

(60) Provisional application No. 61/293,612, filed on Jan. 8, 2010.

(51) Int. Cl.

| | | |
|---|---|---|
| *C07K 16/00* | (2006.01) | |
| *C07K 16/26* | (2006.01) | |
| *A61K 39/395* | (2006.01) | |
| *C07K 16/30* | (2006.01) | |
| *G01N 33/574* | (2006.01) | |

(52) U.S. Cl.
CPC ......... *C07K 16/26* (2013.01); *A61K 39/39558* (2013.01); *C07K 16/303* (2013.01); *G01N 33/57438* (2013.01); *C07K 2317/34* (2013.01); *C07K 2317/73* (2013.01); *G01N 2333/595* (2013.01); *G01N 2800/52* (2013.01)

(58) Field of Classification Search
None
See application file for complete search history.

(56) References Cited

U.S. PATENT DOCUMENTS 6,548,066 B1   4/2003 Michaeli et al.
2011/0117086 A1*  5/2011 Pannequin et al. ........ 424/133.1

FOREIGN PATENT DOCUMENTS

| WO | 2006/032980 A1 | 3/2006 |
|---|---|---|
| WO | WO 2007/135542 A1 | 11/2007 |
| WO | 2008/063479 A2 | 5/2008 |
| WO | 2008/076454 A1 | 6/2008 |

OTHER PUBLICATIONS

Fundamental Immunology p. 242 (William E. Paul, M.D. ed., 3d ed; 1993).*
Rudikoff (Rudikoff, et al., Proc. Natl. Acad. Sci. USA, 79: 1979-1983, 1979).*
Casset (Casset, et al, Biochem. Biophys. Res. Commun. 307(1): 198-205, 2003).*
Holm (Holm, et al., Mol. Immunol. 44(6): 1075-1084, 2007).*
MacCallum et al. (J. Mol. Biol. Oct. 11, 1996; 262 (5): 732-745).*
Lippincott-Schwartz (Current Protocols in Cell Biology, 16.0.1-16.0.2, 2002).*
Rengifo-Cam et al (Current Pharmaceutical Design, 10: 2345-2358, 2004).*
Smith et al (Gastro., 131:1463-1474, 2006).*
Bardram, L., 1990, "Progastrin in Serum from Zollinger-Ellison Patients an Indicator of Malignancy?", *Gastroenterology* 98(6):1420-1426.
Konturek et al., 2006, "Effects of Cyclooxygenase-2 Inhibition on Serum and Tumor Gastrins and Expression of Apoptosis-Related Proteins in Colorectal Cancer," *Dig Diseases and Sci* 51(4): 779-787.
Siddheshwar et al., 2001, "Plasma levels of progastrin but not amidated gastrin or glycine extended gastrin are elevated in patients with colorectal carcinoma," *Gut* 48(1): 47-52.
International Search Report from related International Application No. PCT/EP2011/000049 dated Jul. 4, 2011.
Goetze et al., 2000, "Closing the Gastrin Loop in Pancreatic Carcinoma: Coexpression of Gastrin and its Receptor in Solid Human Pancreatic Adenocarcinoma," *Cancer* 88(11):2487-2494.
Caplin et al., 2000, "Expression and Processing of Gastrin in Pancreatic Adenocarcinoma," *British Journal of Surgery* 87(8):1035-1040.
Matters et al., 2009, "Growth of Human Pancreatic Cancer is Inhibited by Down-Regulation of Gastrin Gene Expression," retrieved from the Internet: URL:http://www.ncbi.nlm.nih.gov/pmc/articles/PMC2704379/pdf/nihms107791.pdf [retrieved on Mar. 2, 2011].
Smith et al., 1995, "Identification of Gastrin as a Growth Peptide in Human Pancreatic Cancer," *American Journal of Physiology* 268(1):R135-R141.
Partial International Search Report from related International Application No. PCT/EP2011/000049 dated Apr. 6, 2011.

* cited by examiner

*Primary Examiner* — Brad Duffy
(74) *Attorney, Agent, or Firm* — Dechert LLP

(57) ABSTRACT

The present disclosure is directed to methods of treating pancreatic cancer in subject using cancer with antibodies that specifically bind to progastrin.

10 Claims, 47 Drawing Sheets

FIG. 1

Figure 4:
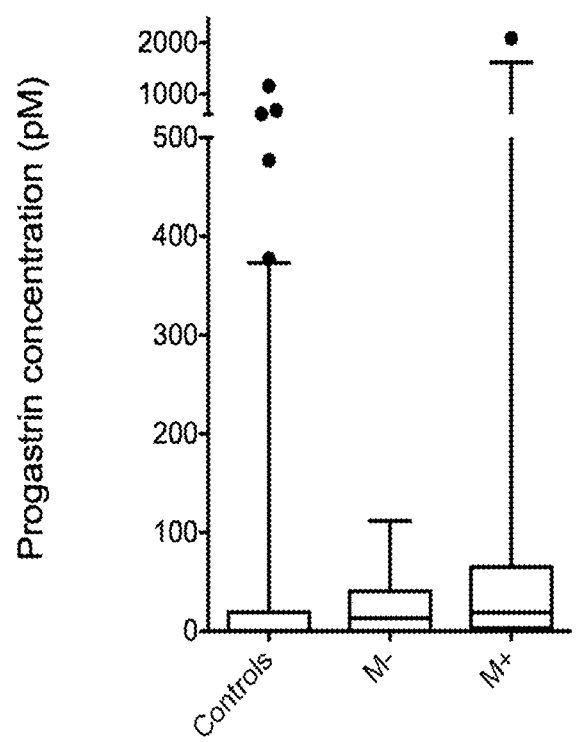

```
Preprogastrin:  M QRLCVYVLIF ALALAAFSEA SWKPRSQQPD APLGTGANRD LELPWLEQQG
               -21        -11         -1  +1              11          21
                PASHHRRQLG PQGPPHLVAD PSKKQGPWLE EEEEAYGWMD FGRRSAEDEN
                31         41         51         61         71

Progastrin:                            SWKPRSQQPD APLGTGANRD LELPWLEQQG
                                       +1              11          21
                PASHHRRQLG PQGPPHLVAD PSKKQGPWLE EEEEAYGWMD FGRRSAEDEN
                31         41         51         61         71

G34:                   QLG PQGPPHLVAD PSKKQGPWLE EEEEAYGWMD F-NH₂
                           41         51         61         71

G34-Gly:               QLG PQGPPHLVAD PSKKQGPWLE EEEEAYGWMD FG
                           41         51         61         71

G17:                                      QGPWLE EEEEAYGWMD F-NH₂
                                          51     61         71

G17-Gly:                                  QGPWLE EEEEAYGWMD FG
                                          51     61         71

CTFP:                                                          SAEDEN
                                                               75
```

FIG. 2A mV$_H$ MAb3

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
                20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
                35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
        50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
                100                 105                 110 gtc tcc tca                                                        345
Val Ser Ser
        115
```

FIG. 2B mV$_L$ MAb3

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt    96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt   288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa   336
Ser His Val Pro Phe Thr Phe Gly Gly Gly Thr Lys Leu Glu Ile Lys
                100                 105                 110
```

FIG. 2C mV$_H$ MAb4

```
cag gtt cag ttg cag cag tct gga gct gag ctg atg aag cca ggg gcc    48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc    96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
            35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
        50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
                100                 105                 110 ctg gtc act gtc tct gca                                           354
Leu Val Thr Val Ser Ala
            115
```

FIG. 2D mV$_L$ MAb4

```
gat ctt gtg atg acc caa act cca ctc tcc ctg cct gtc agt ctt gga    48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt    96
Asp Gln Ala Ser Ile Ser Cys Arg Ser Ser Gln Ser Leu Val His Ser
                20                  25                  30 agt gga gtc acc tat tta cat tgg tac ctg cag aag cca ggc cag tct   144
Ser Gly Val Thr Tyr Leu His Trp Tyr Leu Gln Lys Pro Gly Gln Ser
            35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt   288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa   336
Thr His Val Pro Pro Thr Phe Gly Ser Gly Thr Lys Leu Glu Ile Lys
            100                 105                 110
```

FIG. 2E mV$_H$ MAb8

```
gaa gtg cag ctg gtg gag tct ggg gga ggc tta gtg aag cct gga ggg    48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat    96
Ser Leu Lys Leu Ser Cys Ala Ala Ser Gly Phe Thr Phe Thr Thr Tyr
            20                  25                  30 gcc atg tct tgg gtt cgc cag act ccg gag aag agg ctg gag tgg gtc   144
Ala Met Ser Trp Val Arg Gln Thr Pro Glu Lys Arg Leu Glu Trp Val
            35                  40                  45 gca acc att agt agt ggt ggt act tac acc tac tat cca gac agt gtg   192
Ala Thr Ile Ser Ser Gly Gly Thr Tyr Thr Tyr Tyr Pro Asp Ser Val
        50                  55                  60 aag ggt cga ttc acc atc tcc aga gac aat gcc aag aac gcc cta tac   240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt   288
Leu Gln Met Ser Ser Leu Arg Ser Glu Asp Thr Ala Met Tyr Tyr Cys
            85                  90                  95 gca aca cag ggg aat tac tct ttg gac ttc tgg ggc caa ggc acc tct   336
Ala Thr Gln Gly Asn Tyr Ser Leu Asp Phe Trp Gly Gln Gly Thr Ser
            100                 105                 110 ctc aca gtc tcc tca                                               351
Leu Thr Val Ser Ser
            115
```

FIG. 2F mV$_L$ MAb8

```
gac att gtg atg acg cag gct gca tcc tct aat cca gtc act ctt gga    48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act    96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct   144
Lys Gly Ile Thr Phe Leu Tyr Trp Tyr Leu Gln Lys Pro Gly Gln Ser
            35                  40                  45 cct cag ctc ctg att tat cag atg tcc aac ctt gcc tca gga gtc cca   192
Pro Gln Leu Leu Ile Tyr Gln Met Ser Asn Leu Ala Ser Gly Val Pro
        50                  55                  60 gac agg ttc agt agc agt ggg tca gga act gat ttc aca ctg aga atc   240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat   288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa   336
Leu Glu Leu Pro Leu Thr Phe Gly Ala Gly Thr Lys Leu Glu Leu Lys
            100                 105                 110
```

FIG. 2G mV$_H$ MAb13

```
gag gtg cag ctg gtg gag tct ggg gga ggc ttg gtg cag cct gga ggg    48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat    96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc   144
Gly Met Ser Trp Val Arg Gln Ser Pro Asp Arg Arg Leu Glu Leu Val
            35                  40                  45 gca agt att aat act ttt ggt gat aga acc tat tat cca gac agt gtg   192
Ala Ser Ile Asn Thr Phe Gly Asp Arg Thr Tyr Tyr Pro Asp Ser Val
        50                  55                  60 aag ggc cga ttc acc atc tcc aga gac aat gcc aag aac acc ctg tac   240
Lys Gly Arg Phe Thr Ile Ser Arg Asp Asn Ala Lys Asn Thr Leu Tyr
65                  70                  75                  80 ctg caa atg acc agt ctg aag tct gag gac aca gcc att tat tac tgt   288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc   336
Ala Arg Gly Thr Gly Thr Tyr Trp Gly Gln Gly Thr Thr Leu Thr Val
                100                 105                 110 tcc tca                                                             342
Ser Ser
```

FIG. 2H mV_L MAb13

```
gat gtt gtg ctg acc cag act cca ctc act ttg tcg gtt acc att gga    48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt    96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct   144
Asp Gly Lys Thr Tyr Leu Asn Trp Leu Leu Gln Arg Pro Gly Gln Ser
            35                  40                  45 cca aag cgc cta atc tat ctg gtg tct aaa ctg gac tct gga gtc cct   192
Pro Lys Arg Leu Ile Tyr Leu Val Ser Lys Leu Asp Ser Gly Val Pro
            50                  55                  60 gac agg ttc act ggc agt gga tca ggg aca gat ttc aca ctg aaa atc   240
Asp Arg Phe Thr Gly Ser Gly Ser Gly Thr Asp Phe Thr Leu Lys Ile
65                      70                  75                  80 agc aga gtg gag gct gag gat ttg gga gtt tat tat tgc tgg caa ggt   288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa   336
Thr His Phe Pro Gln Thr Phe Gly Gly Gly Thr Lys Leu Glu Ile Lys
            100                 105                 110
```

FIG. 2I mV$_H$ MAb16

| | | | | | | | | | | | | | | | | |
|---|---|---|---|---|---|---|---|---|---|---|---|---|---|---|---|---|
| cag | gtc | caa | ctg | cag | cag | tct | ggg | gct | gaa | ctg | gtg | aag | cct | ggg | gct | 48 |
| Gln | Val | Gln | Leu | Gln | Gln | Ser | Gly | Ala | Glu | Leu | Val | Lys | Pro | Gly | Ala | |
| 1 | | | | 5 | | | | | 10 | | | | | 15 | | |

| tca | gtg | aag | ttg | tcc | tgc | aag | gct | tct | ggc | tac | acc | ttc | acc | agc | tac | 96 |
|---|---|---|---|---|---|---|---|---|---|---|---|---|---|---|---|---|
| Ser | Val | Lys | Leu | Ser | Cys | Lys | Ala | Ser | Gly | Tyr | Thr | Phe | Thr | Ser | Tyr | |
| | | 20 | | | | | | 25 | | | | | 30 | | | |

| tat | atg | tac | tgg | gtg | aag | cag | agg | cct | gga | caa | ggc | ctt | gag | tgg | att | 144 |
|---|---|---|---|---|---|---|---|---|---|---|---|---|---|---|---|---|
| Tyr | Met | Tyr | Trp | Val | Lys | Gln | Arg | Pro | Gly | Gln | Gly | Leu | Glu | Trp | Ile | |
| | | 35 | | | | | 40 | | | | | 45 | | | | |

| gga | gag | att | aat | cct | agc | aat | ggt | ggt | act | aac | ttc | aat | gag | aag | ttc | 192 |
|---|---|---|---|---|---|---|---|---|---|---|---|---|---|---|---|---|
| Gly | Glu | Ile | Asn | Pro | Ser | Asn | Gly | Gly | Thr | Asn | Phe | Asn | Glu | Lys | Phe | |
| | 50 | | | | | 55 | | | | | 60 | | | | | |

| aag | agc | aag | gcc | aca | ctg | act | gta | gac | aaa | tcc | tcc | agc | aca | gca | tac | 240 |
|---|---|---|---|---|---|---|---|---|---|---|---|---|---|---|---|---|
| Lys | Ser | Lys | Ala | Thr | Leu | Thr | Val | Asp | Lys | Ser | Ser | Ser | Thr | Ala | Tyr | |
| 65 | | | | | 70 | | | | | 75 | | | | | 80 | |

| atg | caa | ctc | agc | agc | ctg | aca | tct | gag | gac | tct | gcg | gtc | tat | tac | tgt | 288 |
|---|---|---|---|---|---|---|---|---|---|---|---|---|---|---|---|---|
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| aca | aga | ggc | ggt | tac | tac | ccc | ttt | gac | tac | tgg | ggc | caa | ggc | acc | act | 336 |
|---|---|---|---|---|---|---|---|---|---|---|---|---|---|---|---|---|
| Thr | Arg | Gly | Gly | Tyr | Tyr | Pro | Phe | Asp | Tyr | Trp | Gly | Gln | Gly | Thr | Thr | |
| | | | 100 | | | | | 105 | | | | | 110 | | | |

| ctc | aca | gtc | tcc | tca | | | | | | | | | | | | 351 |
|---|---|---|---|---|---|---|---|---|---|---|---|---|---|---|---|---|
| Leu | Thr | Val | Ser | Ser | | | | | | | | | | | | |
| | | 115 | | | | | | | | | | | | | | |

FIG. 2J mV$_L$ MAb16

```
gat gtt gtg atg acc cag act cca ctc act ttg tcg gtt acc att ggg    48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt    96
Arg Pro Ala Ser Ile Ser Cys Lys Ser Ser Gln Ser Leu Leu Asp Ser
                20                  25              30 gat gga aag aca tat ttg tat tgg ttg tta cag agg cca ggc cag tct   144
Asp Gly Lys Thr Tyr Leu Tyr Trp Leu Leu Gln Arg Pro Gly Gln Ser
            35                  40                  45 cca aag cgc cta atc tat ctg gtg tct gag ctg gac tct gga gtc cct   192
Pro Lys Arg Leu Ile Tyr Leu Val Ser Glu Leu Asp Ser Gly Val Pro
        50                  55                  60 gac agg atc act ggc agt ggg tcg ggg aca gat ttc aca ctg aag atc   240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga   288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa   336
Thr His Ser Pro Tyr Thr Phe Gly Gly Gly Thr Lys Leu Glu Ile Lys
            100                 105                 110
```

FIG. 2K mV_H MAb19

```
gat gtg cag ctt cag gag tcg gga cct ggc ctg gtg aaa cct tct cag   48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat   96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg   144
Tyr Ala Trp Asn Trp Ile Arg Gln Phe Pro Gly Asn Lys Leu Glu Trp
                35                  40                  45 atg ggc tac ata agc ttc agt ggt tac act agt tac aac cca tct ctc   192
Met Gly Tyr Ile Ser Phe Ser Gly Tyr Thr Ser Tyr Asn Pro Ser Leu
        50                  55                  60 aaa agt cga atc tct gtc act cgg gac aca tcc agg aac caa ttc ttc   240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt   288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc   336
Ala Arg Glu Val Asn Tyr Gly Asp Ser Tyr His Phe Asp Tyr Trp Gly
                100                 105                 110 caa ggc acc att gtc aca gtc tcc tca                               363
Gln Gly Thr Ile Val Thr Val Ser Ser
        115                 120
```

FIG. 2L mV$_L$ MAb19

```
caa ctt gcg ctc act cag tca tct tca gcc tct ttc tcc ctg gga gcc    48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc    96
Ser Ala Lys Leu Thr Cys Thr Leu Ser Ser Gln His Arg Thr Tyr Thr
                20                  25                  30 att gaa tgg tat cag caa cag tca ctc aag cct cct aag tat gtg atg   144
Ile Glu Trp Tyr Gln Gln Gln Ser Leu Lys Pro Pro Lys Tyr Val Met
            35                  40                  45 gag gtt aag aaa gat gga agc cac agc aca ggt cat ggg att cct gat   192
Glu Val Lys Lys Asp Gly Ser His Ser Thr Gly His Gly Ile Pro Asp
        50                  55                  60 cgc ttc tct gga tcc agt tct ggt gct gat cgc tac ctc agc att tcc   240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat   288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc   336
Ala Ile Lys Gly Gln Ser Val Phe Val Phe Gly Gly Gly Thr Lys Val
                100                 105                 110 act gtc cta                                                       345
Thr Val Leu
        115
```

FIG. 3A hV$_H$ MAb3

Gln Val Gln Leu Val Gln Ser Gly Ala Glu Val Lys Lys Pro Gly Ala
1              5                   10                  15

Ser Val Lys Val Ser Cys Lys Ala Ser Gly Tyr Ile Phe Thr Ser Tyr
              20                  25                  30

Trp Val His Trp Val Arg Gln Ala Pro Gly Gln Arg Leu Glu Trp Met
          35                  40                  45

Gly Gly Phe Tyr Pro Gly Asn Ser Asp Ser Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
              85                  90                  95

Thr Arg Arg Asp Ser Pro Gln Tyr Trp Gly Gln Gly Thr Leu Val Thr
              100                 105                 110

Val Ser Ser
    115

FIG. 3B hV$_L$ MAb3

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25              30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110
```

FIG. 3C hV$_H$ MAb4

Gln Val Gln Leu Val Gln Ser Gly Ala Glu Val Lys Lys Pro Gly Ala
1           5                   10                  15

Ser Val Lys Val Ser Cys Lys Ala Ser Gly Tyr Thr Phe Ser Ser Ser
            20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
                100                 105                 110

Leu Val Thr Val Ser Ser
            115

FIG. 3D hV$_L$ MAb4

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
                20                  25                  30

Ser Gly Val Thr Tyr Leu Tyr Trp Tyr Leu Gln Lys Pro Gly Gln Ser
                35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
                100                 105                 110

FIG. 3E hV$_H$ MAb8(a)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115
```

FIG. 3F hV_L MAb8(a)

Asp Ile Val Met Thr Gln Ser Pro Leu Ser Leu Pro Val Thr Pro Gly
1             5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
        50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
                100                 105                 110

FIG. 3G hV$_H$ MAb8(b)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                      30

Ala Met Asn Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
            115
```

FIG. 3H hV_L MAb8(b)

```
Asp Ile Val Met Thr Gln Ser Pro Leu Ser Leu Pro Val Thr Pro Gly
1            5                    10                  15

Glu Pro Ala Ser Ile Ser Cys Arg Ser Ser Lys Ser Leu Arg His Thr
            20                  25              30

Lys Gly Ile Thr Phe Leu Asp Trp Tyr Leu Gln Lys Pro Gly Gln Ser
            35                  40              45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
                100                 105                 110
```

FIG. 3I hV$_H$ MAb8(c)

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Lys|Pro|Gly|Gly|
|1| | | |5| | | | |10| | | | |15|

Ser Leu Arg Leu Ser Cys Ala Ala Ser Gly Phe Thr Phe Thr Thr Tyr
　　　　　20　　　　　　　　25　　　　　　　　30

Ala Met Ser Trp Val Arg Gln Ala Pro Gly Lys Gly Leu Glu Trp Val
　　　　35　　　　　　　　40　　　　　　　　45

Ser Thr Ile Ser Ser Gly Gly Thr Tyr Thr Tyr Tyr Ala Asp Ser Val
　　50　　　　　　　　55　　　　　　　　60

Lys Gly Arg Phe Thr Ile Ser Arg Asp Asn Ala Lys Asn Ser Leu Tyr
65　　　　　　　　70　　　　　　　　75　　　　　　　　80

Leu Gln Met Asn Ser Leu Arg Ala Glu Asp Thr Ala Val Tyr Tyr Cys
　　　　　　　85　　　　　　　　90　　　　　　　　95

Ala Thr Gln Gly Asn Tyr Ser Leu Asp Phe Trp Gly Gln Gly Thr Thr
　　　　　　100　　　　　　　105　　　　　　　110

Val Thr Val Ser Ser
　　　　115

FIG. 3J hV$_L$ MAb8(c)

Asp Ile Val Met Thr Gln Ser Pro Leu Ser Leu Pro Val Thr Pro Gly
1          5                    10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

FIG. 3K hV$_H$ MAb13(a)

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Thr Gly Thr Tyr Trp Gly Gln Gly Thr Leu Val Thr Val
            100                 105                 110

Ser Ser

FIG. 3L hV<sub>L</sub> MAb13(a)

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
                100                 105                 110
```

FIG. 3M hV$_H$ MAb13(b)

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
            35                  40                  45

Ala Ser Ile Asn Thr Phe Gly Asp Arg Thr Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

FIG. 3N hV<sub>L</sub> MAb13(b)

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25              30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110
```

FIG. 3O hV$_H$ MAb16(a)

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

FIG. 3P hV_L MAb16(a)

Asp Val Val Met Thr Gln Ser Pro Leu Ser Leu Pro Val Thr Leu Gly
1              5                    10                       15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Asn Arg Asp Ser Gly Val Pro
      50                  55                  60

Asp Arg Phe Ser Gly Ser Gly Ser Gly Thr Asp Phe Thr Leu Lys Ile
65                  70                  75                       80

Ser Arg Val Glu Ala Glu Asp Val Gly Val Tyr Tyr Cys Trp Gln Gly
            85                  90                       95

Thr His Ser Pro Tyr Thr Phe Gly Gln Gly Thr Lys Leu Glu Ile Lys
            100                 105                 110

FIG. 3Q hV$_H$ MAb16(b)

Gln Val Gln Leu Val Gln Ser Gly Ala Glu Val Lys Lys Pro Gly Ala
1            5                      10                    15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65              70                  75                      80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

FIG. 3R hV$_L$ MAb16(b)

Asp Val Val Met Thr Gln Ser Pro Leu Ser Leu Pro Val Thr Leu Gly
1             5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                      95

Thr His Ser Pro Tyr Thr Phe Gly Gln Gly Thr Lys Leu Glu Ile Lys
            100                 105                 110

FIG. 3S hV<sub>H</sub> MAb16(c)

Gln Val Gln Leu Val Gln Ser Gly Ala Glu Val Lys Lys Pro Gly Ala
1                5                    10                   15

Ser Val Lys Val Ser Cys Lys Ala Ser Gly Tyr Thr Phe Thr Ser Tyr
         20                  25                      30

Tyr Met Tyr Trp Val Arg Gln Ala Pro Gly Gln Gly Leu Glu Trp Met
         35                   40                  45

Gly Glu Ile Asn Pro Ser Asn Gly Gly Thr Asn Tyr Ala Gln Lys Phe
     50                  55                   60

Gln Gly Arg Val Thr Met Thr Arg Asp Thr Ser Thr Ser Thr Val Tyr
65                   70                  75                   80

Met Glu Leu Ser Ser Leu Arg Ser Glu Asp Thr Ala Val Tyr Tyr Cys
             85                  90                       95

Thr Arg Gly Gly Tyr Tyr Pro Phe Asp Tyr Trp Gly Gln Gly Thr Thr
             100                 105                  110

Val Thr Val Ser Ser
         115

FIG. 3T hV$_L$ MAb16(c)

Asp Val Val Met Thr Gln Ser Pro Leu Ser Leu Pro Val Thr Leu Gly
1            5                    10                   15

Gln Pro Ala Ser Ile Ser Cys Arg Ser Ser Gln Ser Leu Leu Asp Ser
            20                  25                   30

Asp Gly Lys Thr Tyr Leu Tyr Trp Phe Gln Gln Arg Pro Gly Gln Ser
            35                  40                   45

Pro Arg Arg Leu Ile Tyr Leu Val Ser Glu Arg Asp Ser Gly Val Pro
            50                  55                   60

Asp Arg Phe Ser Gly Ser Gly Ser Gly Thr Asp Phe Thr Leu Lys Ile
65                      70                  75                   80

Ser Arg Val Glu Ala Glu Asp Val Gly Val Tyr Tyr Cys Trp Gln Gly
                85                  90                   95

Thr His Ser Pro Tyr Thr Phe Gly Gln Gly Thr Lys Leu Glu Ile Lys
            100                 105                  110

FIG. 3U hV$_H$ MAb19(a)

Gln Val Gln Leu Gln Glu Ser Gly Pro Gly Leu Val Lys Pro Ser Gln
1               5                       10                      15

Thr Leu Ser Leu Thr Cys Thr Val Ser Gly Tyr Ser Ile Thr Ser Asp
            20                  25                      30

Tyr Ala Trp Asn Trp Ile Arg Gln His Pro Gly Lys Gly Leu Glu Trp
        35                      40                  45

Ile Gly Tyr Ile Ser Phe Ser Gly Tyr Thr Tyr Tyr Asn Pro Ser Leu
        50                  55                      60

Lys Ser Arg Val Thr Ile Ser Val Asp Thr Ser Lys Asn Gln Phe Ser
65                  70                  75                      80

Leu Lys Leu Ser Ser Val Thr Ala Ala Asp Thr Ala Val Tyr Tyr Cys
                85                  90                      95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

FIG. 3V hV$_L$ MAb19(a)

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
    115

FIG. 3W hV$_H$ MAb19(b)

Gln Val Gln Leu Gln Glu Ser Gly Pro Gly Leu Val Lys Pro Ser Gln
1           5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
            35                  40                  45

Ile Gly Tyr Ile Ser Phe Ser Gly Tyr Thr Tyr Tyr Asn Pro Ser Leu
        50              55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120

FIG. 3X hV$_L$ MAb19(b)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Gln Pro Glu Lys Gly Pro Arg Tyr Leu Met
            35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

FIG. 3Y hV$_H$ MAb19(c)

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
        50              55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

FIG. 3Z hV_L MAb19(c)

Gln Leu Val Leu Thr Gln Ser Pro Ser Ala Ser Ala Ser Leu Gly Ala
1              5                    10                  15

Ser Val Lys Leu Thr Cys Thr Leu Ser Ser Gln His Arg Thr Tyr Thr
              20                  25                  30

Ile Glu Trp His Gln Gln Pro Glu Lys Gly Pro Arg Tyr Leu Met
         35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
              85                  90                  95

Ala Ile Lys Gly Gln Ser Val Phe Val Phe Gly Gly Gly Thr Lys Val
              100                 105                 110

Glu Ile Lys
       115

METHODS FOR TREATING PANCREATIC CANCER

1. REFERENCE TO RELATED APPLICATIONS

This application claims the benefit under 35 U.S.C. §119 (e) of provisional application No. 61/293,612, filed Jan. 8, 2010, the content of which is incorporated by reference in its entirety.

2. REFERENCE TO SEQUENCE LISTING, TABLE OR COMPUTER PROGRAM

The Sequence Listing concurrently submitted herewith under 37 CFR §1.821 in a computer readable form (CRF) via EFS-Web as file name "BR007USSEQLIST.txt" is incorporated herein by reference. The electronic copy of the Sequence Listing was created on Dec. 28, 2010, with a file size of 77.9 Kbytes.

3. FIELD OF THE INVENTION

The present disclosure is directed to, among other things, methods of treating subjects with primary and/or metastatic pancreatic cancer by administering to the subject a composition comprising an antibody specific for progastrin.

4. BACKGROUND

Despite decades of basic and clinical research, cancer remains one of mankind's greatest scourges. According to statistics collected by the World Health Organization, cancer is one of the leading causes of death worldwide, having killed 7.4 million people in 2004, or about 13% of all deaths that year. While much has been learned regarding what causes cancer, and how cancer works at the molecular level, the greatest reductions in cancer death rates remain attributable to public health interventions, such as anti-smoking campaigns, and earlier diagnosis made possible by advances in imaging technology and molecular diagnostics. When it comes to the hard work of actually killing cancer cells, however, clinicians still rely on therapeutic modalities, such as surgery, radiation and chemotherapy, that would have been familiar to oncologists of a generation ago. Although the efficacy of all these treatments has improved over the years, the improvement in cure rates and the increase in longevity has been incremental. Even the new targeted therapies resulting from the revolution in molecular oncology have, for the most part, improved outcomes modestly.

Pancreatic cancer, a malignant neoplasm of the pancreas, is a particularly challenging form of cancer to treat, as it typically goes undetected until no longer treatable ((Jemal et al., 2008, CA Cancer J. Clin. 58(2):71-96)). The prognosis is poor-fewer than 5% of those diagnosed with pancreatic cancer are still alive 5 years after diagnosis ((Jemal et al., 2010, CA Cancer J. Clin. 60(5):277-300)), and complete remission is rare ((Ghaneh et al., 2007, Gut 56(8):1134-1152)). The median survival from diagnosis is only 3-6 months ((Stathis & Moore, 2010, Nat. Rev. Clin. Oncol. 7(3):163-172)). It has been estimated that in 2010, about 43,000 individuals in the United States alone will be diagnosed with pancreatic cancer, and that about 36,800 will die from the disease (see, www.cancer.gov/cancertopics/types/pancreatic). Although pancreatic cancer accounts for only 2.5% of new cancer cases diagnosed each year, it is responsible for 6% of yearly cancer deaths ((Jemal et al., 2007, Cancer J. Clin. 57(1):43-46)), representing one of the highest fatality rates of all cancers. Indeed, in the United States, pancreatic cancer is the fourth-highest cancer killer amongst men and women.

Another challenging aspect of managing cancer is treating patients in whom cells from the primary (original) tumor have broken free and migrated to another location within the body, typically through the lymph or blood, via a process called "metastasis," to form another, metastatic (or secondary) tumor. The secondary or metastatic tumor is typically of the same type as the original tumor, regardless of its new location, such that the disease is referred to as metastatic cancer, and not cancer of the new resident tissue. For example, pancreatic cancer that has spread to the liver is metastatic pancreatic cancer, not liver cancer. Since primary pancreatic cancer is often not diagnosed until a late stage, the incidence of metastasis is high. Indeed, approximately 80% of patients already have metastasis at the time of diagnosis ((Sohn et al., 2000, J. Gastrointest. Surg. 4(6):567-579)).

Metastasis limits treatment options, as resection or removal of the primary tumor is no longer a sufficient treatment option. Gemcitabine-based chemotherapy currently represents the standard of care for any patient with metastatic disease. Survival of patients with metastatic disease treated with gemcitabine is only about 6 months (ranging from 4.0 to 7.1 months, depending upon the study). Current trials with combination treatments, for example gemcitabine with chemotherapy (oxaliplatine, 5-FU or irinotecan), or gemcitabine with targeted therapy (erlontinib, bevacizumab or cetuximab) report only a 1 to 2 month gain in survival ((Sathis & Moore, 2000, Nat. Rev. Clin. Oncol. 7(3):163-172)).

While moderate advances in the treatment options for primary pancreatic cancer and metastatic pancreatic cancer have been made in recent years (see, Id.), there remains a pressing need for alternative and/or more effective therapies.

5. SUMMARY

Gastrin is a gut peptide hormone that stimulates secretion of gastric acid. In adult mammals, it is produced principally by G cells in the gastric antrum, and to some extent in the upper small intestine and pancreas. Referring to FIG. 1, the gastrin gene is translated into a 101-amino acid polypeptide, called "preprogastrin" which contains a signal sequence (underlined) that is cleaved, giving rise to progastrin ("PG"), an 80-amino acid residue polypeptide. Gastrin, which is found primarily in three forms, G34, G17 and G14 (not illustrated), results from progastrin processing.

The presence of amidated gastrin has been observed in pancreatic tumors ((Goetze et al., 2000, Cancer 88(11):2487-2494)) and researchers have tried to use anti-gastrin approaches to treat pancreatic tumors (see, e.g., Chau et al., 2006, Br. J. Cancer 94:1107-1115; Brett et al., 2002, J. Clin. Oncol. 20:4225-4231). It has also been observed that patients suffering from pancreatic cancer have detectable levels of progastrin in their pancreatic tumors ((Caplin et al., 2000, Br. J. Surg. 87(8):1035-1040)). It has now been discovered that anti-progastrin approaches can be used to diagnose, monitor and treat both primary and metastatic pancreatic cancer. As demonstrated for the first time herein, patients with both primary and metastatic pancreatic cancer have elevated plasma and/or serum levels of progastrin, and the proliferation of cell lines derived from primary and metastatic pancreatic tumors is inhibited when treated with antibodies that specifically bind progastrin, as are their abilities to form cancer spheres under low adherence conditions. These discoveries provides powerful new tools to diagnose, treat, prevent recurrence of, and monitor the course of progression and/or treatment of pancreatic cancer.

Accordingly, in one aspect, the present disclosure provides methods of treating pancreatic cancer, which can be primary pancreatic cancer or metastatic pancreatic cancer, that involves administering to a subject diagnosed with primary or metastatic pancreatic cancer an amount of an antibody that specifically binds progastrin ("anti-PG antibody") effective to provide therapeutic benefit. The anti-PG antibody may be administered alone as monotherapy, or in conjunction with, or adjunctive to, other treatment modalities, such as tumor resection, radiation therapy, chemotherapy, etc.

When used in conjunction with, or adjunctive to, tumor resection, the anti-PG antibody may be administered before and/or after removal of the tumor, and may be continued for a specific period of time following tumor removal, until a plasma and/or serum progastrin level below a specified threshold level is achieved, or until a decrease in plasma and/or serum progastrin levels over a specified period of time is achieved.

When used in conjunction with, or adjunctive to, chemotherapy, the anti-PG antibody may be administered prior to chemotherapy, concomitant with chemotherapy, or after chemotherapy. Again, the anti-PG antibody may be administered for a specified period of time, until a plasma and/or serum progastrin level below a specified threshold level is achieved, or until a decrease in plasma and/or serum progastrin levels or a specified period of time is achieve.

As will be discussed in more detail below, patients diagnosed with primary and/or metastatic pancreatic cancer have elevated plasma and/or serum levels of PG. For example, with reference to FIG. 4, serum and/or plasma levels of progastrin in healthy individuals are typically negligible. Individuals suffering from pancreatic cancer have measureable levels of about 50 pM. This discovery results in several useful and important new tools in the diagnosis and management of pancreatic cancer.

First, since pancreatic cancer can be difficult to diagnose, measured PG plasma and/or serum levels can be used in conjunction with other diagnostic tests to either confirm a diagnosis of pancreatic cancer, or aid in the initial diagnosis. For example, it is commonly known that the signs of pancreatic cancer, when present, are similar to signs of many other illnesses. Common symptoms include pain in the upper abdomen that radiates to the back, loss of appetite and/or nausea and vomiting, significant weight loss, and painless jaundice. Less common symptoms include distal vein thrombosis and pulmonary embolism, diabetes mellitus and pancreatitis. Since early detection provides greater treatment options and better prognosis, plasma and/or serum PG levels could be measured in patients presenting with these and/or other symptoms of pancreatic cancer to aid diagnosis, where an elevated level, for example a plasma and/or serum level at or above about 50 pM, would indicate the patient has pancreatic cancer.

Measuring plasma and/or serum PG levels to aid diagnosis may be particularly useful in subjects exhibiting risk factors for pancreatic cancer, including but not limited to, smoking, dietary and environmental factors, infection with *H. pylori*, metabolic syndromes (e.g., obesity, impaired glucose tolerance, long-standing diabetes) and family history, which accounts for approximately 5-10% of patients with pancreatic cancer ((Maisonneuve & Lowenfels, 2010, Dig. Dis. 28(4-5):645-656)). Plasma and/or serum PG levels in subjects exhibiting such or other risk factors could be periodically monitored, with observed increases over time, or an observed level at or above a threshold of about 50 pM indicating the individual may be developing pancreatic cancer. Such monitoring of individuals at risk could aid in early detection of the disease, providing better treatment options.

Second, measured plasma and/or serum PG levels can be used to monitor the effectiveness of any pancreatic cancer therapy, including the anti-PG therapies described herein, and/or potential recurrence or metastases. While not intending to be bound by any particular theory of operation, it is expected that, as the tumors shrink over the course of therapy, plasma and/or serum PG levels will decrease, and may return to normal.

Thus, in another aspect, the disclosure provides methods useful for diagnosing and/or monitoring efficacy of treatment and/or recurrence of pancreatic cancer, whether primary pancreatic cancer or metastatic pancreatic cancer, in a subject. The method generally comprises measuring a plasma and/or serum level of PG in a relevant subject, either at a distinct point in time, or over a period of time, and determining whether the level is above or below a threshold level, or increases or decreases over time. Levels above a threshold level, or levels that increase over time in subjects at risk of developing pancreatic cancer, or in subjects exhibiting one or more symptoms associated with pancreatic cancer, is indicative that the subject has pancreatic cancer. Levels below a threshold level, or that decrease over time, are indicative that the particular therapy is effective. In view of the short survival time of patients having pancreatic cancer, the measurements should be taken reasonably often, for example once every two weeks, or even at shorter intervals.

6. BRIEF DESCRIPTION OF THE FIGURES

FIG. 1 provides amino acid sequences of human preprogastrin (SEQ ID NO:100), where the signal peptide sequence is underlined, mature human progastrin (SEQ ID NO:20) and certain products of progastrin processing, including G34 (SEQ ID NO:102), G34-Gly (SEQ ID NO:103), G17 (SEQ ID NO:104), G17-Gly (SEQ ID NO:105) and CTFP (SEQ ID NO:106).

FIG. 2. provides polynucleotide and amino acid sequences of variable light and variable heavy chains of certain exemplary murine anti-hPG monoclonal antibodies. In each case, the three CDRs are shown in bolded-underlined text. Specifically:

FIG. 2A provides the polypeptide sequence of the $V_H$ chain of murine anti-hPG MAb3 (SEQ ID NO:12) and a polynucleotide sequence encoding it (SEQ ID NO:16);

FIG. 2B provides the polypeptide sequence of the $V_L$ chain of murine anti-hPG MAb3 (SEQ ID NO:13) and a polynucleotide sequence encoding it (SEQ ID NO:17);

FIG. 2C provides the polypeptide sequence of the $V_H$ chain of murine anti-hPG MAb4 (SEQ ID NO:14) and a polynucleotide sequence encoding it (SEQ ID NO:18);

FIG. 2D provides the polypeptide sequence of the $V_L$ chain of murine anti-hPG MAb4 (SEQ ID NO:15) and a polynucleotide sequence encoding it (SEQ ID NO:19);

FIG. 2E provides the polypeptide sequence of the $V_H$ chain of murine anti-hPG MAb8 (SEQ ID NO:59) and a polynucleotide sequence encoding it (SEQ ID NO:67);

FIG. 2F provides the polypeptide sequence of the $V_L$ chain of murine anti-hPG MAb8 (SEQ ID NO:63) and a polynucleotide sequence encoding it (SEQ ID NO:71);

FIG. 2G provides the polypeptide sequence of the $V_H$ chain of murine anti-hPG MAb13 (SEQ ID NO:60) and a polynucleotide sequence encoding it (SEQ ID NO:68);

FIG. 2H provides the polypeptide sequence of the $V_L$ chain of murine anti-hPG MAb13 (SEQ ID NO:64) and a polynucleotide sequence encoding it (SEQ ID NO:72);

FIG. 2I provides the polypeptide sequence of the $V_H$ chain of murine anti-hPG MAb16 (SEQ ID NO:61) and a polynucleotide sequence encoding it (SEQ ID NO:69);

FIG. 2J provides the polypeptide sequence of the $V_L$ chain of murine anti-hPG MAb16 (SEQ ID NO:65) and a polynucleotide sequence encoding it (SEQ ID NO:73);

FIG. 2K provides the polypeptide sequence of the $V_H$ chain of murine anti-hPG MAb19 (SEQ ID NO:62) and a polynucleotide sequence encoding it (SEQ ID NO:70); and FIG. 2L provides the polypeptide sequence of the $V_L$ chain of murine anti-hPG MAb19 (SEQ ID NO:66) and a polynucleotide sequence encoding it (SEQ ID NO:74).

FIG. 3 provides projected polypeptide sequences for humanized variable heavy and light chains of selected anti-hPG monoclonal antibodies described herein. In each case, the three CDRs are shown in bolded-underlined text. Specifically:

FIG. 3A provides the projected amino acid sequence of the $V_H$ chain of humanized MAb3 (SEQ ID NO:21);

FIG. 3B provides the projected amino acid sequence of the $V_L$ chain of humanized MAb3 (SEQ ID NO:22);

FIG. 3C provides the projected amino acid sequence of the $V_H$ chain of humanized MAb4 (SEQ ID NO:23);

FIG. 3D provides the projected amino acid sequence of the $V_L$ chain of humanized MAb4 (SEQ ID NO:24);

FIG. 3E provides the projected amino acid sequence of the $V_H$ chain of humanized MAb8(a) (SEQ ID NO:75);

FIG. 3F provides the projected amino acid sequence of the $V_L$ chain of humanized MAb8(a) (SEQ ID NO:76);

FIG. 3G provides the projected amino acid sequence of the $V_H$ chain of humanized MAb8(b) (SEQ ID NO:77);

FIG. 3H provides the projected amino acid sequence of the $V_L$ chain of humanized MAb8(b) (SEQ ID NO:78);

FIG. 3I provides the projected amino acid sequence of the $V_H$ chain of humanized MAb8(c) (SEQ ID NO:79);

FIG. 3J provides the projected amino acid sequence of the $V_L$ chain of humanized MAb8(c) (SEQ ID NO:76);

FIG. 3K provides the projected amino acid sequence of the $V_H$ chain of humanized MAb13(a) (SEQ ID NO:80);

FIG. 3L provides the projected amino acid sequence of the $V_L$ chain of humanized MAb13(a) (SEQ ID NO:81);

FIG. 3M provides the projected amino acid sequence of the $V_H$ chain of humanized MAb13(b) (SEQ ID NO:82);

FIG. 3N provides the projected amino acid sequence of the $V_L$ chain of humanized MAb13(b) (SEQ ID NO:83);

FIG. 3O provides the projected amino acid sequence of the $V_H$ chain of humanized MAb16(a) (SEQ ID NO:84);

FIG. 3P provides the projected amino acid sequence of the $V_L$ chain of humanized MAb16(a) (SEQ ID NO:85);

FIG. 3Q provides the projected amino acid sequence of the $V_H$ chain of humanized MAb16(b) (SEQ ID NO:86);

FIG. 3R provides the projected amino acid sequence of the $V_L$ chain of humanized MAb16(b) (SEQ ID NO:87);

FIG. 3S provides the projected amino acid sequence of the $V_H$ chain of humanized MAb16(c) (SEQ ID NO:88);

FIG. 3T provides the projected amino acid sequence of the $V_L$ chain of humanized MAb16(c) (SEQ ID NO:89);

FIG. 3U provides the projected amino acid sequence of the $V_H$ chain of humanized MAb19(a) (SEQ ID NO:90);

FIG. 3V provides the projected amino acid sequence of the $V_L$ chain of humanized MAb19(a) (SEQ ID NO:91);

FIG. 3W provides the projected amino acid sequence of the $V_H$ chain of humanized MAb19(b) (SEQ ID NO:92);

FIG. 3X provides the projected amino acid sequence of the $V_L$ chain of humanized MAb19(b) (SEQ ID NO:93);

FIG. 3Y provides the projected amino acid sequence of the $V_H$ chain of humanized MAb19(c) (SEQ ID NO:94); and FIG. 3Z provides the projected amino acid sequence of the $V_L$ chain of humanized MAb19(c) (SEQ ID NO:95).

FIG. 4 provides a graph illustrating progastrin concentrations in plasma or serum from patients with primary (M−) or metastatic (M+) pancreatic cancer, as compared to healthy controls.

Figure 5:
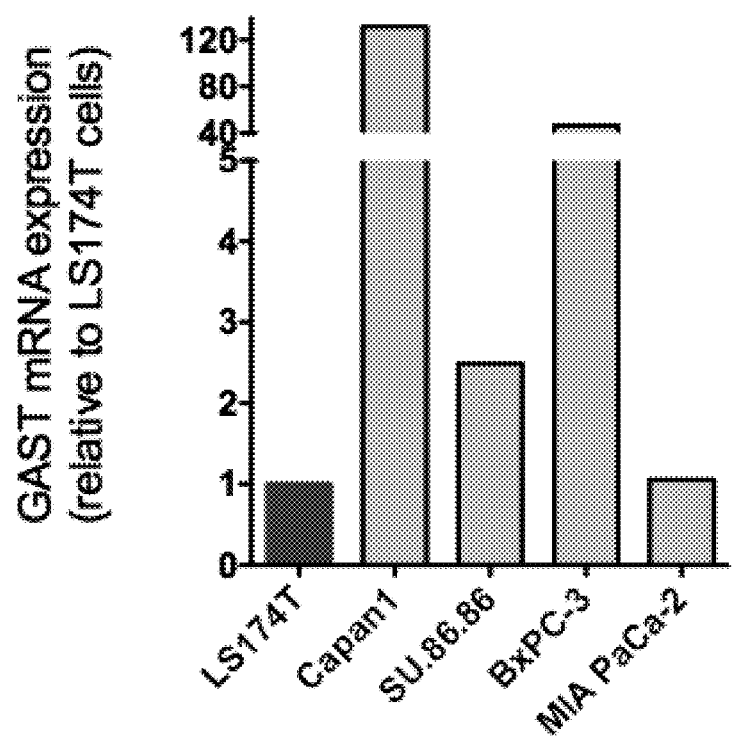

FIG. 5 provides a graph illustrating the expression levels of progastrin in various types of primary and metastatic pancreatic cancer cell lines.

Figure 6:
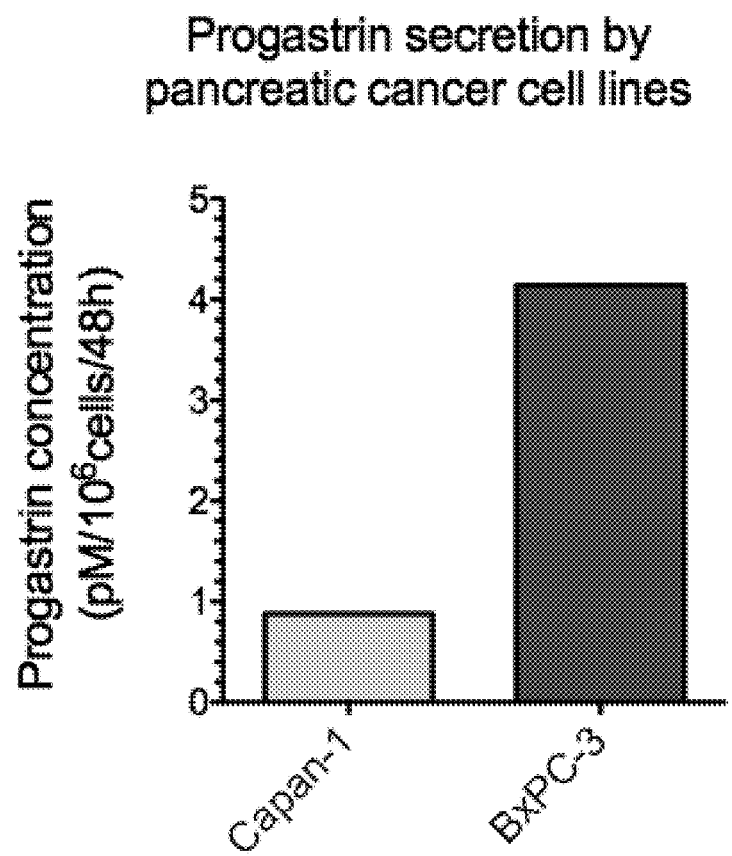

FIG. 6 provides a graph illustrating progastrin secretion by various types of primary and metastatic pancreatic cancer cell lines.

Figure 7:
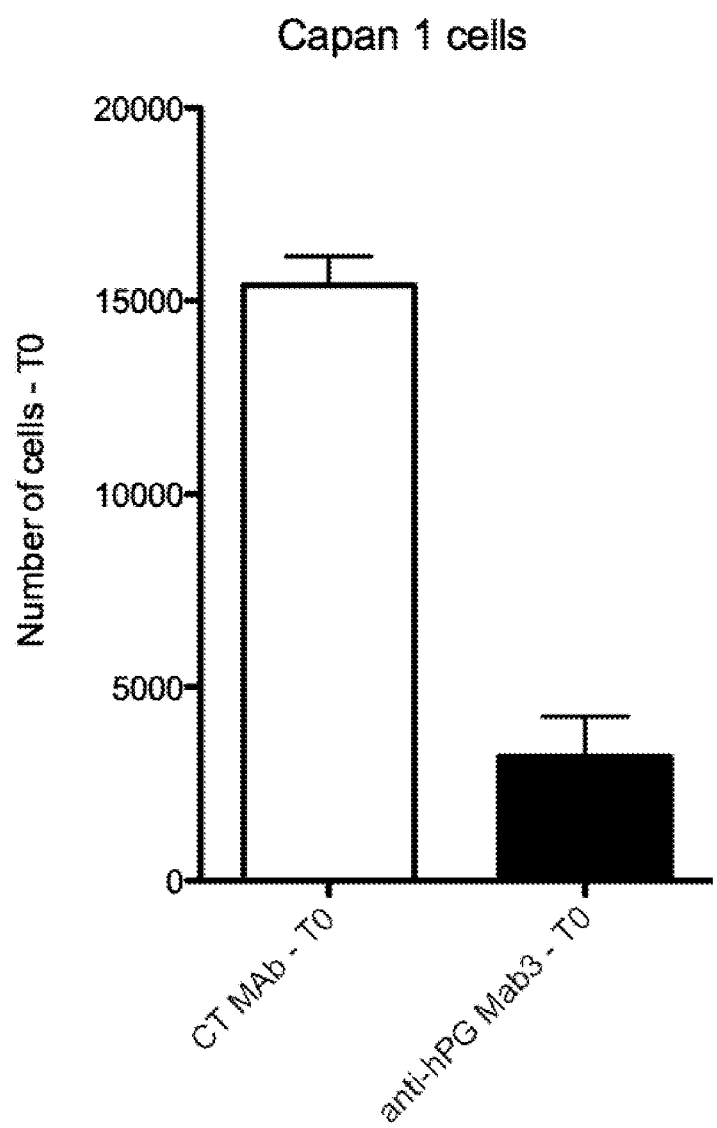

FIG. 7 provides a graph comparing the anti-proliferative properties of exemplary anti-hPG MAb3 on Capan 1 cells (metastatic pancreatic tumor cells) as compared to a negative control monoclonal antibody.

Figure 8:
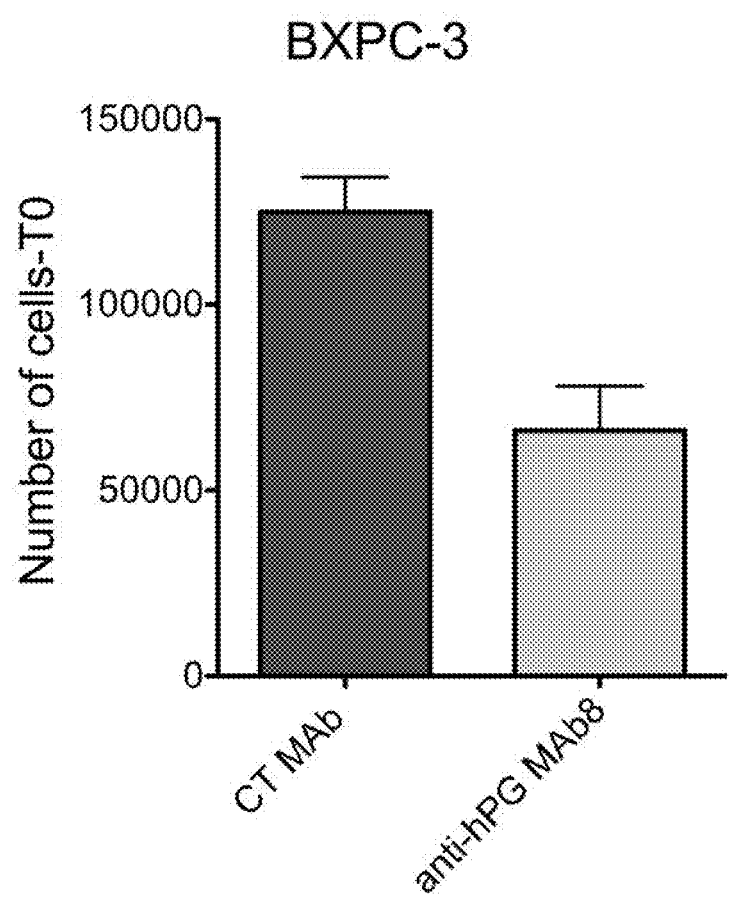

FIG. 8 provides a graph comparing the anti-proliferative properties of exemplary anti-hPG MAb8 on BxPC-3 cells (primary pancreatic tumor cells) as compared to a negative control monoclonal antibody.

Figure 9:
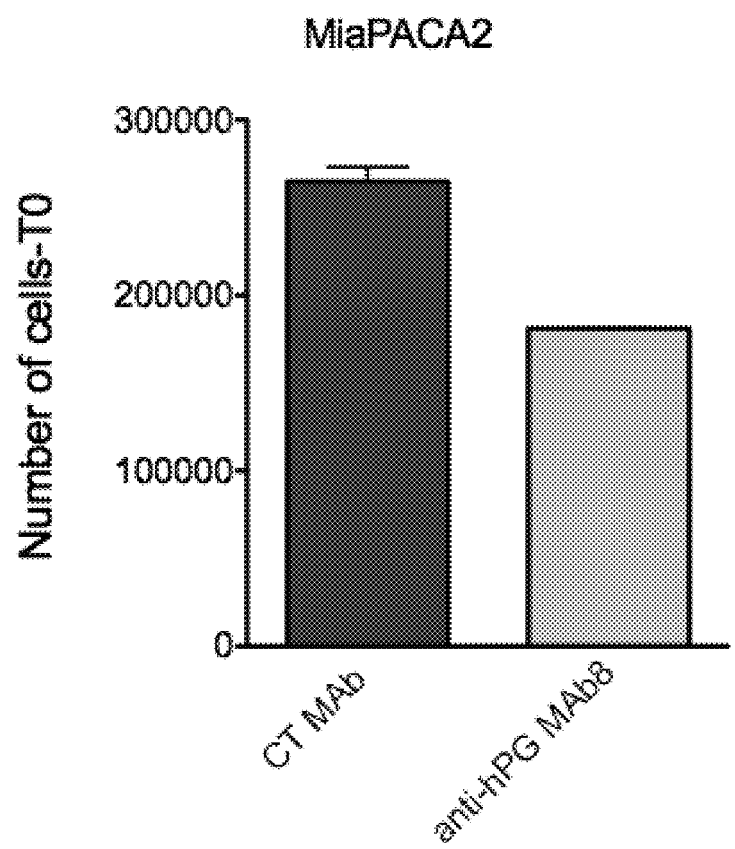

FIG. 9 provides a graph comparing the anti-proliferative properties of exemplary anti-hPG MAb8 on MIA PaCa2 cells (primary pancreatic tumor cells) as compared to a negative control monoclonal antibody.

Figure 10:
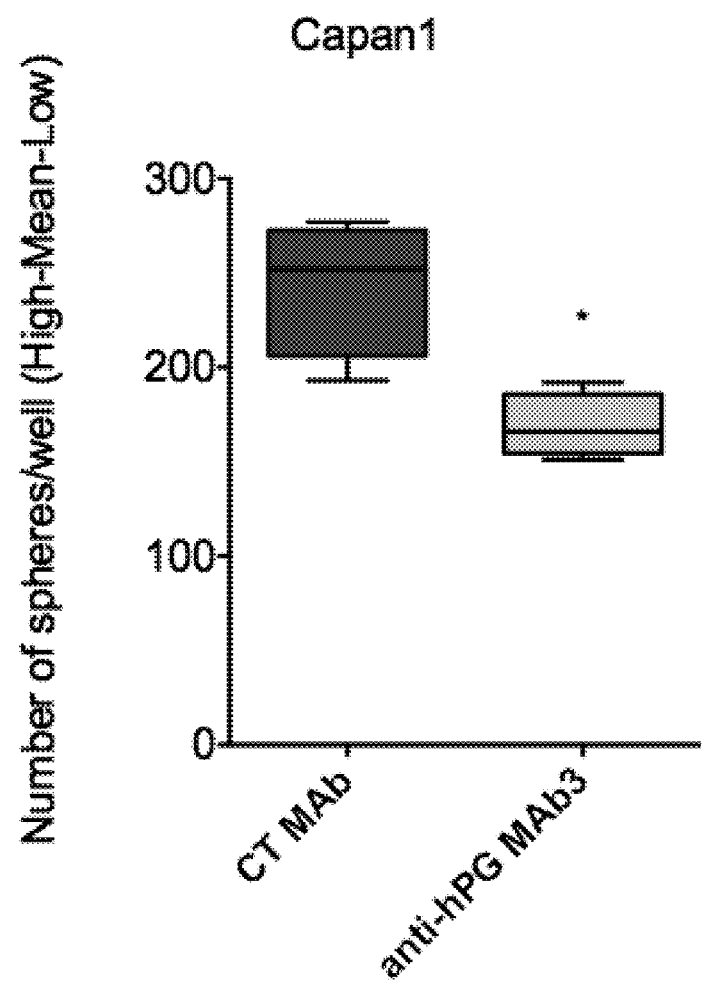

FIG. 10 provides a graph demonstrating the inhibitory property of exemplary anti-hPG MAb3 on the long-term capacity of Capan 1 cells (metastatic pancreatic tumor cells) to form cancer spheres in low adherence conditions as compared to untreated control cells.

Figure 11:
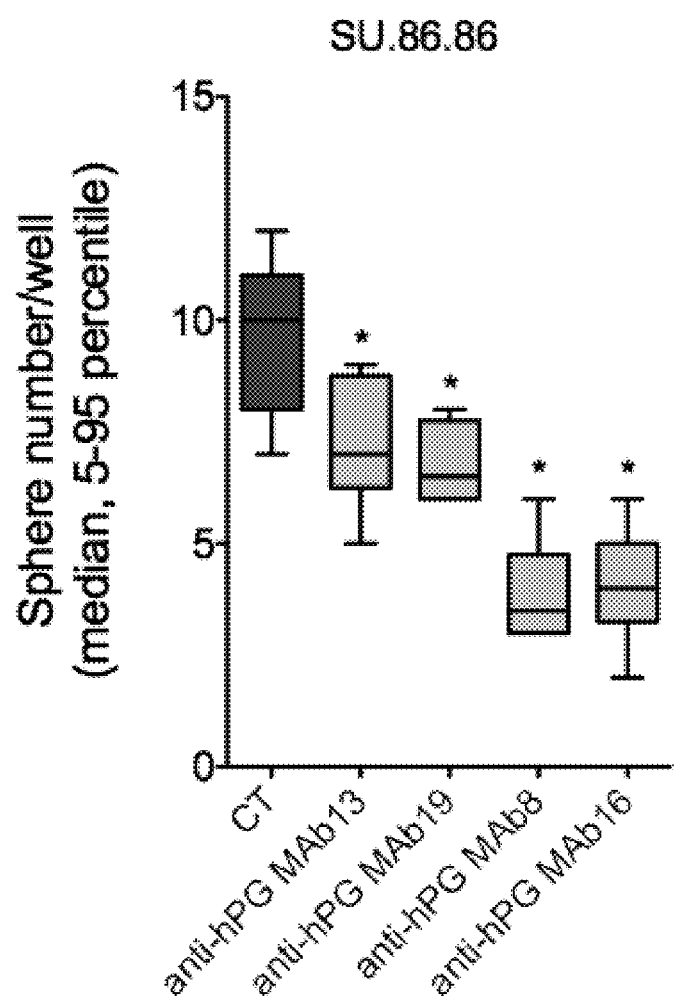

FIG. 11 provides a graph demonstrating the inhibitory properties of exemplary anti-hPG MAb8, MAb13, MAb16, and MAb19 on the long-term capacity of SU.86.86 cells (metastatic pancreatic tumor cells) to form cancer spheres in low adherence conditions as compared to untreated control cells.

7. DETAILED DESCRIPTION

7.1 Pancreatic Cancer

The pancreas, a thin gland about six inches in length, has two main functions: to product juices that help digest food and to produce hormones, such as an insulin and glucagon, that help control blood sugar levels. The digestive juices are produced by exocrine pancreatic cells, and the hormones by endocrine pancreatic cells. Approximately 95% or more of pancreatic cancers originate in exocrine cells ((Yao et al., 2007, Oncology 14(12):3492-3450)). Of the exocrine pancreatic cancers, approximately 95% are adenocarcinomas, with the remaining 5% including adenosquamous carcinomas, signet ring cell carcinomas, hepatoid carcinomas, colloid carcinomas, undifferentiated carcinomas, and undifferentiated carcinomas with oesteaclast-like giant cells (see, http://pathology.jhu.edu/pancreas/BasicTypes1.php).

Early pancreatic cancer often does not cause symptoms ((Jemal et al., 2008, CA Cancer J. Clin. 58(2):71-96)), and symptoms caused by later stage pancreatic cancer are usually varied and non-specific ((Stathis & Moore, 2010, Nat. Rev. Clin. Oncol. 7(3):163-172)). As a consequence, pancreatic cancer is often not diagnosed until it is advanced ((Jemal et al., 2008, CA Cancer J. Clin. 58(2):71-96)). Common symptoms include, but are not limited to, pain in the upper abdominal and back pain, loss of appetite and/or nausea and vomiting, significant weight loss, painless jaundice, distal vein thrombosis, pulmonary embolism, as well as diabetes mellitus and/or pancreatitis.

Various risk factors are associated with pancreatic cancer, and include, but are not limited to, smoking; long-standing diabetes; chronic pancreatitis; and certain hereditary conditions, such as hereditary pancreatitis, multiple endocrine neoplasia type 1 syndrome, hereditary non-polyposis colon cancer (HNPCC; Lynch syndrome), von-Hippel-Lindau syndrome, ataxia-talangiectasia, and the familial atypical multiple mole melanoma syndrome (FAMMM).

Diagnostic procedures used to diagnose pancreatic cancer include imaging studies such as computed tomography (CT) scanning, magnetic resonance imaging (MRI), positron emission tomography (PET) scanning, endoscopic ultrasound (EUS), laparoscopy, endoscopic retrograde cholangiopancreatography (ERCP) and percutaneous transhepatic cholangiography (PTC), but the definitive diagnosis is made by endoscopic needle biopsy or surgical excision of radiologically suspicious tissue. These various diagnostic techniques are also used to stage the cancer, which affects treatment options. The following stages are commonly used to assess pancreatic cancer:

Stage 0 (carcinoma in situ): In this stage, abnormal cells are found in the lining of the pancreas. These abnormal cells may become cancerous and spread to surrounding tissue.

Stage I: In this stage, cancer has formed and is found in the pancreas only. Stage I is further divided into two substages, depending upon the size of the tumor: Stage IA (tumor is 2 cm or smaller) and Stage IB (tumor is larger than 2 cm).

Stage II: In this stage, the cancer has spread to nearby tissues and organs, and may have spread to lymph nodes. This stage is further divided into substages based on where the cancer has spread. Stage IA (spread to nearby tissue and organs but not lymph); and Stage IIB (spread to lymph and possibly other nearby tissues and organs).

Stage III: In this stage, the cancer has spread to the major blood vessels near the pancreas, and may also have spread to nearby lymph nodes.

Stage IV: In this stage, the cancer may be of any size, and has spread to distant tissues and organs, such as the liver, lung, and peritoneal cavity (i.e., the cancer has metastasized).

There are three main treatment options (surgery, radiation therapy and chemotherapy), which vary by stage. Treatments for Stage I and Stage II primary pancreatic cancer may include surgery, with adjuvant chemotherapy based on gemcitabine or on a 5-FU regimen, with or without radiation therapy.

Often times, primary pancreatic cancer recurs following treatment (called recurrent pancreatic cancer). Gemcitabine-based chemotherapy is also generally used for patients with recurrent and locally advanced pancreatic cancer, sometimes followed by radiation or by chemoradiation 7.2 Metastasis As noted in the Background Section, metastasis refers to a process by which cancer spreads. Briefly, tumor cells leave a primary tumor, travel via the blood circulation or lymphatic system to a new tissue site, and form a secondary tumor. The tumors at the new tissue site are referred to as metastatic tumors, and typically identify the source of the primary tumor. For example, pancreatic cancer that has spread to other tissues is referred to as "metastatic pancreatic cancer," despite the tissue location of the secondary, metastatic tumor.

Cancer cells frequently spread to lymph nodes near the primary tumor, which is called lymph node involvement or regional disease.

Metastasis consists of a number of distinct steps: invasion and migration, intravasation, circulation, extravasation and colonization, proliferation and angiogenesis. During invasion and migration, individual cells detach from the primary tumor and invade adjacent, healthy tissue. To accomplish this, the tumor cells must become motile, and are hypothesized to undergo a phenotypic transformation, called an epithelial to mesenchymal transition. Kalluri et al., 2009, J. Clin. Invest. 119(6):1420-28. In addition, such cells often produce enzymes that degrade the extracellular matrix, thereby facilitating migration out of the primary tumor and into the surrounding healthy tissue. When a tumor cell encounters a blood or lymphatic vessel, it inserts itself between the endothelial cells lining the vessels and penetrates into the blood stream or lymphatic system. The aberrant tumor cell then travels via the circulatory system or lymphatic system to a new organ or to a lymph node. The tumor cell may then lodge in the capillaries or lymphatics of an organ, such as liver, lung, or other tissue or organ, and then extravasate by penetrating the endothelium into the tissue space. Finally, during colonization, proliferation and angiogenesis, the tumor cells take up residence in their new host tissue and begin to grow. When the new metastatic tumor reaches sufficient size, it may secrete growth factors, such as VEGF, to stimulate the growth of new blood vessels into the tumor so as to supply oxygen and nutrition to the fast growing tumor.

Tumors can spread via metastasis to almost any part of the body. Local recurrence, liver metastases, and peritoneal spread are the most common sites of recurrence after resection of pancreatic tumors. Typical loco-regional invasion is found in the retropancreatic neural tissue, duodenum, portal vein (PV), and superior mesenteric vein (SMV), or regional lymph nodes. The most usual sites of distant metastases in pancreatic cancer are the liver and peritoneal cavity. Other less common sites are the lung, bone, and brain. Unusual sites such as muscle, skin, heart, pleura, stomach, umbilicus, kidney, appendix, spermatic cord, and prostate have also been reported ((Howard, 1996, Curr. Prob.l Cancer 20(5): 281-328; Borad et al., 2009, Yale J. Biol. Med. 82(1):1-6))

7.3 Treatment for Primary and Metastatic Pancreatic Cancer

Patients diagnosed with pancreatic cancer typically have a poor prognosis, in part because pancreatic cancer usually causes no symptoms early on, leading to locally advanced or metastatic disease at the time of diagnosis. Treatment options, discussed above, depend upon the stage of the disease at diagnosis.

7.4 Anti-hPG Antibodies and their Effect on Primary and Metastatic Pancreatic Cancer As disclosed herein, it has been reported that subjects with pancreatic cancer have detectable levels of progastrin in their pancreatic tumors ((Caplin et al., 2000, Br. J. Surg. 87(8):1035-1040)). Data reported herein and discussed in the Examples Section demonstrate that pancreatic cancer cell lines BxPC-3, MIA PaCa-2, Capan 1 and SU.86.86 express the mRNA for the progastrin-encoding gene (GAST) (Example 7), and also that pancreatic cancer cell lines secrete progastrin (Example 8). It has now been discovered that patients with both primary and metastatic pancreatic cancer have elevated plasma and/or serum levels of progastrin (Example 6), that the growth of cells derived from primary and metastatic pancreatic tumors is inhibited by treatment with antibodies that specifically bind human progastrin ("hPG") (Examples 9, 10 and 11) and that the capacity of pancreatic cancer cells to grow as tumor spheres under low adherence culture conditions is significantly reduced following pre-treatment with anti-hPG antibodies (Example 12). Based on these surprising and encouraging discoveries, it is expected that such anti-hPG antibodies may be used to aid diagnosis of pancreatic cancer, monitor the efficacy of a pancreatic cancer treatment regimen, treat pancreatic cancer of any stage of development, including both primary and metastatic pancreatic cancer, and prevent recurrence of pancreatic cancer.

As recently demonstrated by Hollande et al., progastrin stimulates the beta-catenin/Tcf-4 pathway of colorectal cancer cells by suppressing ICAT, a negative regulator of beta-catenin/Tcf-4 signaling (see, WO 2007/135542). Beta-catenin/Tcf-4 signaling causes cells to proliferate. In the absence of this signaling, they differentiate and undergo a normal cell cycle, including programmed cell death, or apoptosis. Hollande et al. have also demonstrated that exposing such cells to anti-hPG antibodies blocks beta-catenin/Tcf-4-induced proliferation, and that the growth or proliferation of CRC cells is inhibited (see, e.g., WO 2007/135542). Cells that proliferate in response to treatment with or exposure to progastrin, whether endogenously produced or exogenous, and in which proliferation is inhibited upon treatment with or exposure to anti-PG antibodies, are referred to herein as "progastrin-sensitive."

As noted above, it has been discovered that both primary and metastatic tumor cells are progastrin-sensitive, and respond to treatment with or exposure to anti-PG antibodies. While not intending to be bound by any theory of operation, it is believed that anti-PG antibodies exert their anti-proliferative properties by binding PG and blocking its interaction with its putative receptor, in turn repressing beta-catenin/Tcf-4-induced proliferation that results from increased ICAT expression. Other mechanisms by which anti-PG antibodies may interfere with the survival and/or growth of primary and/or metastatic cancer cells are also possible, and are not intended to limit the scope of the inventions disclosed herein.

7.5 Therapeutic Methods

Accordingly, in one aspect, the present disclosure provides methods of treating a subject suffering from or diagnosed with pancreatic cancer. The method involves administering to the subject an amount of one or more anti-PG antibody(ies) effective to provide therapeutic benefit. Anti-PG antibodies generally, and specific anti-PG antibodies useful in the methods, are described in detail in a later section.

The subject treated may be any animal, for example, a mammal, such as a farm animal (e.g., a cow, pig, horse, etc.) or a domesticated pet (e.g., dog, cat, etc.), or a human. The anti-PG antibody administered should be specific for the species of animal being treated. For treatment of human subjects, the anti-PG antibody(ies) should specifically bind human progastrin (referred to herein as "anti-hPG antibodies," described in more detail, below).

The pancreatic cancer being treated can be in any stage of development, from Stage 0, to Stage I, Stage II, Stage III, or even Stage IV. Indeed, a significant advantage of the anti-PG therapy described herein is that it is expected to be effective against metastatic pancreatic tumors as well as primary pancreatic tumors, thereby providing benefit to patients having pancreatic cancer even in late stages of development. It is also expected to prevent recurrence of pancreatic cancer.

The anti-PG therapy can be used alone, as monotherapy, or in combination with or adjunctive to other therapies commonly used to treat the particular stage of pancreatic cancer. Such common treatments are noted above, and include chemotherapy with, for example, gemcitabine, 5-FU or other chemotherapeutic agents, and targeted therapies, such as treatment with bevacizumab. In a specific embodiment, the anti-PG therapy is applied in combination with, or adjunctive to, treatment with other antibodies targeting tumor cells, such as bevacizumab. When used in combination with other treatments, the anti-PG antibody(ies) and other therapy can be administered simultaneously, successively, or separately.

As used herein, an anti-hPG antibody and a second therapeutic agent are said to be administered successively if they are administered to the patient on the same day, for example during the same patient visit. Successive administration can occur 1, 2, 3, 4, 5, 6, 7, 8 or more hours apart. In contrast, the anti-PG antibody and a second therapeutic agent are said to be administered separately if they are administered to the patient on different days. For example, the anti-PG antibody and the second therapeutic agent can be administered at 1-day, 2-day, 3-day, 4-day, 5-day, 6-day, one-week, 2-week or monthly intervals. Administration of the anti-PG antibody can precede or follow administration of the second therapeutic agent.

Alternatively, the anti-PG antibody and second therapeutic agent can be administered concurrently for a period of time, followed by a second period of time in which the administration of the anti-PG antibody and the second therapeutic agent is alternated.

Similarly, the anti-PG antibody can be administered in combination with, or adjunctive to, surgical removal of the tumor(s), if possible. The anti-PG antibody(ies) may be administered before, during or after removal of the tumor.

7.6 Pharmaceutical Compositions

The anti-PG antibody(ies) will typically be administered in the form of pharmaceutical formulations or compositions. Such formulations or compositions may optionally include additional active and/or therapeutic agents, as is known in the art. The formulations will typically include a pharmaceutically acceptable carrier, excipient or diluent. The specific carriers, excipients and/or diluents used will depend upon the desired mode of administration. The composition can be in any suitable form depending upon the desired method of administering it to a patient.

The anti-PG antibodies can be administered to a subject by a variety of routes, typically parenterally, for example, via subcutaneous, intravenous, intraperitoneal or intramuscular injection. Administration can be effected as one or more bolus injections, or as one or more infusions. Other routes of administration are also possible in accordance with the knowledge of those ordinarily skilled in the art. The most suitable route for administration in any given case will depend on the particular antibody, the subject, and the stage of the pancreatic cancer being treated.

Pharmaceutical compositions can be conveniently presented in unit dose forms containing a predetermined amount of an anti-PG antibody per dose. Such a unit can contain for example but without limitation 5 mg to 5 g, for example 10 mg to 1 g, or 20 to 50 mg.

Pharmaceutical compositions can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml. Surfactants have a tendency, however, to bind to antibodies, and can compromise their conformations. Therefore, when used, stabilizing concentrations should be low and discerned experimentally.

Additional miscellaneous excipients can include chelating agents (e.g., EDTA), antioxidants (e.g., ascorbic acid, methionine, vitamin E), and cosolvents.

7.7 Effective Dosages

The anti-PG antibodies are administered to the subject in an amount sufficient or effective to provide a therapeutic benefit. In the context of treating primary and/or metastatic pancreatic cancer, a therapeutic benefit can be inferred if one or more of the following is achieved: halting or slowing the growth of tumors, reducing the numbers and/or sizes of tumors within a patient, shrinking inoperable tumors to a size and location such that they can be removed surgically, increasing life expectancy, and/or improving patient quality of life.

A complete cure, while desirable, is not required for therapeutic benefit to exist. Indeed, since the median survival from diagnosis of pancreatic cancer is only 3-6 months ((Stathis & Moore, 2010, Nat Rev Clin Oncol. 7(3):163-72)), an increase in survival of an individual of an additional 3 months beyond this median provides considerable therapeutic benefit. See, e.g., Philip et al., 2009, J. Clin. Oncol. 24(33):5660-5669.

In some contexts, therapeutic benefit can be correlated with one or more surrogate end points, in accordance with the knowledge of one of ordinary skill in the art. By way of example and not limitation, plasma and/or serum PG concentrations can be measured in a subject over time, with a reduction in PG levels, or a level below a threshold level, for example, below about 50 pM, 40 pM, 30 pM, 20 pM, 10 pM or 5 pM, being indicative of therapeutic benefit.

Tumor size, number and metabolism can be measured using various scanning techniques, such as, but not limited to, CT, MRI, functional MRI, SPECT and PET, as well as other methods known to those of ordinary skill in the art.

Binding all free PG is not required to achieve therapeutic efficacy, although it may be desirable. Free PG means PG that is available to be bound by an anti-PG antibody. Rather, reducing the concentration of free PG within or around tumors, systemically, in particular body fluids, or elsewhere, to a more limited extent may also be effective. Exemplary tissues and body fluids in which free PG concentration may be reduced by administration of anti-PG antibody(ies) compositions include, but are not limited to, tumor samples removed from a patient, ascites fluid, fluid from pleural effusions, cerebrospinal fluid, lymph, blood, plasma, serum and others. The concentration of PG in one or more of these tissues or body fluids can be quantified using an ELISA technique or other techniques familiar to those of ordinary skill in the art.

In accordance with the knowledge of those ordinarily skilled in the art, the dose of an anti-PG antibody can be titrated in a patient so as to reduce the free PG concentration in a tissue or body fluid of interest at a predetermined time after administration at least about 10%, 20%, 30%, 40%, 50%, 60%, 70%, 80%, 90, or 100%, or about 5%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-95%, or a percentage reduction in free PG concentration ranging between any of the foregoing values.

The amount of anti-PG antibody administered will depend on a variety of factors, including the stage of pancreatic cancer being treated, the form, route and site of administration, the therapeutic regimen (e.g., whether a second therapeutic agent is used), the age and condition of the particular subject being treated, the sensitivity of the patient being treated to anti-PG antibodies. The appropriate dosage can be readily determined by a person skilled in the art. Ultimately, a clinician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using conventional techniques known to those of ordinary skill in the art.

Effective dosages can be estimated initially from in vitro assays. For example, an initial dose for use in animals may be formulated to achieve a circulating blood or serum concentration of anti-PG antibody that is at or above the binding affinity constant of the particular anti-PG antibody. Calculating dosages to achieve such circulating blood or serum concentrations taking into account the bioavailability of the particular antibody is well within the capabilities of skilled artisans. For guidance, the reader is referred to Part 1: General Principles in "Goodman and Gilman's The Pharmacological Basis of Therapeutics," 11th Ed., Hardman, J. G., et al., Eds., McGraw-Hill Professional, and the references cited therein.

Initial dosages can also be estimated from in vivo data, such as animal models. Animal models useful for testing the efficacy of agents to treat pancreatic cancer are well known in the art. Skilled artisans can routinely adapt such information to determine dosages suitable for human administration.

In specific embodiments, an i.v. dose may be determined for an individual subject by measuring the serum or plasma PG concentration of the individual a few times a few days to a few weeks prior to treatment and calculating an amount of anti-PG antibody that would be saturating, i.e., an amount that would be sufficient to bind all of the PG. As will be appreciated by skilled artisans, the amount of any specific antibody necessary to achieve saturation for a given serum or plasma concentration of PG will depend, in part, on the affinity constant of the particular antibody. Methods for calculating saturating quantities for specific anti-PG antibodies of interest are well-known.

To insure saturation, an amount that is greater than the calculated saturating amount may be administered, for example, at least 2-, 3-, 4-, 5-, 6-, 7-, 8-, 9- or even 10-fold greater than the calculated saturating amount may be administered. For modes of administration other than i.v., the amount can be adjusted based upon pharmacokinetic and bioavailability, as is well known in the art.

The effective dose of an anti-PG antibody is expected to range from about 0.001 mg/kg to about 250 mg/kg per single (e.g., bolus) administration, multiple administrations or continuous (e.g., infusion) administration, or any effective range or value therein depending on the stage of pancreatic cancer being treated, the route of administration and the age, weight and condition of the subject. In certain embodiments, each dose can range from about 0.1 mg/kg to about 0.5 mg/kg; about 0.25 mg/kg to about 0.75 mg/kg; about 0.5 mg/kg to about 1 mg/kg; about 2 mg/kg; about 1.5 mg/kg to about 2.5 mg/kg; about 2 mg/kg to about 3 mg/kg; about 2.5 mg/kg to about 3.5 mg/kg; about 3 mg/kg to about 4 mg/kg; about 3.5 mg/kg to about 4.5 mg/kg; about 4 mg/kg to about 5 mg/kg; about 5 mg/kg to about 7 mg/kg; about 6 mg/kg to about 8 mg/kg; about 7 mg/kg to about 9 mg/kg; about 8 mg/kg to about 10 mg/kg; about 10 mg/kg to about 15 mg/kg; about 12.5 mg/kg to about 17.5 mg/kg; about 15 mg/kg to about 20 mg/kg; about 17.5 mg/kg to about 22.5 mg/kg; about 20 mg/kg to about 25 mg/kg; about 22.5 mg/kg to about 27.5 mg/kg; about 25 mg/kg to about 30 mg/kg; about 30 mg/kg to about 40 mg/kg; about 35 mg/kg to about 45 mg/kg; about 40 mg/kg to about 50 mg/kg; about 45 mg/kg to about 55 mg/kg; about 50 mg/kg to about 60 mg/kg; about 55 mg/kg to about 65 mg/kg; about 60 mg/kg to about 70 mg/kg; about 65 mg/kg to about 75 mg/kg; about 70 mg/kg to about 80 mg/kg; about 75 mg/kg to about 85 mg/kg; about 80 mg/kg to about 90 mg/kg; about 85 mg/kg to about 95 mg/kg; about 90 mg/kg to about 100 mg/kg; about 95 mg/kg to about 105 mg/kg; about 100 mg/kg to about 150 mg/kg; about 125 mg/kg to about 175 mg/kg; about 150 mg/kg to about 200 mg/kg; about 175 mg/kg to about 225 mg/kg; about 200 mg/kg to about 250 mg/kg. Other dosage ranges are also possible.

Amount, frequency, and duration of administration will depend on a variety of factors, such as the patient's age, weight, and disease condition. Thus, in non-limiting examples, a therapeutic regimen for administration can continue for 1 day or more, 2 days or more, 3 days or more, 4 days or more, 5 days or more, 6 days or more, 1 week or more, 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of anti-PG antibody can be administered as a single dose or over the course of a therapeutic regimen, e.g., over the course of a week, two weeks, three weeks, one month, three months, six months, one year, or longer.

7.8 Methods of Diagnosis and Patient Monitoring to Determine Therapeutic Efficacy As noted above, patients diagnosed with primary and/or metastatic pancreatic cancer have elevated plasma and/or serum levels of PG. Referring to FIG. 4, the baseline levels of PG in healthy individuals are negligible, typically being at the limit of detection. PG plasma and/or serum levels in subjects with primary and/or metastatic pancreatic cancer are measureable, and are about 50 pM. Based on this observation, plasma and/or serum levels of PG can be used to aid the diagnosis of, or monitor the effectiveness of treatments of, primary or metastatic pancreatic cancer.

Accordingly, the present disclosure also provides methods of diagnosing, or monitoring the efficacy of a course of treatment of primary or metastatic pancreatic cancer. To aid diagnosis, the PG level of a plasma or serum sample from the individual undergoing diagnosis can be measured and compared to a threshold value, with a level higher than the threshold being indicative of pancreatic cancer, especially where other diagnostic tests indicate the individual may be suffering from pancreatic cancer. In some embodiments, a plasma or serum PG concentration of at least about 50 pM is indicative of pancreatic cancer, especially when combined with other positive test results.

For purposes of monitoring efficacy of therapy, blood, plasma or serum PG levels can be measured at specified time points. A decrease in concentration over time, and/or a measured level below a threshold value at a particular point in time, is indicative of efficacy. The threshold value may be that discussed above, or could be a subject-specific value obtained from the subject being treated prior to initiation of therapy, or at some point early during a round therapy.

Without wishing to be bound by any particular theory of operation, it is believed that as the numbers and/or sizes of tumors in a patient are reduced as a result of the round of therapy, the total amount of PG produced by the tumors also declines. By contrast, no substantial change, or a rise in PG levels after a round of therapy is completed, may indicate that the therapy was not effective. This information can be used by care providers to decide whether a new round of therapy should be started.

PG levels can be measured using analytical techniques familiar to those of ordinary skill in the art, such as, but not limited to, RIA and ELISA. Anti-hPG antibodies useful for measuring PG levels of human subjects are described in a later section.

In a specific embodiment, PG levels may be measured using a sandwich ELISA with one anti-PG antibody targeting the N-terminus of progastrin and a second anti-PG antibody targeting the C-terminus of progastrin. Exemplary N- and C-terminal anti-PG antibodies useful for such a sandwich assay are described in a later section. In such an assay, a surface, such as the wells in a 96-well plate, is prepared to which a known quantity of a first, "capture," N-terminal or C-terminal anti-PG antibody is bound. A test sample is then applied to the surface followed by an incubation period. The surface is then washed and a solution containing a second, "detection," anti-PG antibody is applied, where the detection antibody binds a different epitope of PG (for example, if the capture antibody is a C-terminal anti-PG antibody, an N-terminal anti-PG antibody is used as the detection antibody, and vice versa). PG levels are then measured either directly (if, for example, the detection antibody is conjugated to a detectable label) or indirectly (through a labeled secondary antibody that binds the detection anti-PG antibody). For this assay, antibodies should be used in excess such that all PG is bound and quantified. A specific sandwich assay for measuring plasma and/or serum PG levels is provided in Example 1.

Multiple measurements at different intervals after the completion of therapy may be taken, and then graphed to determine if a trend exists. In a non-limiting example, PG levels can be determined weekly or monthly for the first six months after a round of therapy is concluded. Other intervals are also possible.

In an embodiment involving a round of therapy using an anti-PG antibody, one or more measurements may also be taken during the course of therapy so that the effect of the antibodies on PG levels can be estimated. In other such embodiments, where residual anti-PG antibodies are present in a patient during sampling, the data may show a reduction in PG levels, due to sequestration of PG by the antibodies, followed by a rise, as this effect abates, followed by a subsequent decline, if the treatment was effective. In yet other embodiments, post-therapy measurements can be taken after it is estimated that the anti-PG antibodies have been cleared from the patient so that binding of PG by such antibodies does not affect the accuracy of the measurement of PG concentration.

Different baselines may be used against which to compare PG levels detected in a patient. In some embodiments, the baseline is established by previous measurements from the same patient, which may be taken at predetermined intervals. In a non-limiting example, PG levels can be determined weekly or monthly for the first six months after the end of treatment, then every three months until the second anniversary of the end of treatment, and then every six months or year thereafter. Other intervals are also possible.

In other embodiments, the baseline can be established from average PG levels in a population of patients with characteristics similar to those of the patient undergoing monitoring. Such characteristics may include, but are not necessarily limited to sex, age, primary cancer type, exposure to certain types of treatments, any combination of these, and others. In yet other embodiments, more than one baseline can be used in the monitoring of a particular patient. For example, both a patient-specific baseline, as well as a population-derived baseline can be used.

In some embodiments, where the average PG concentration in a formerly treated cancer patient is in the normal range for the relevant population to which the patient is being compared, and remains steady, the patient would be scored as not having metastases, and thus does not require new treatment. By contrast, where the PG concentration is seen to rise over a period of time in a formerly treated cancer patient, and in certain embodiments, exceed a threshold derived from population data, the patient may be scored as possibly having metastases, and thus be a candidate for new treatment against metastatic cancer.

Because eating usually increases gastrin synthesis and secretion, it may also cause transient increases in blood PG levels, which may interfere with the accurate measurement of PG levels in patients being monitored for therapeutic efficacy, and for the presence of metastases. To avoid this effect, particularly where PG concentration in blood samples is to be determined, samples can be taken from the patient after fasting.

7.9 Anti-PG Antibodies

Antibodies useful in the methods disclosed herein are those that specifically bind human progastrin over other products of the gastrin gene. Referring to FIG. 1, the gastrin gene is translated into a 101-amino acid polypeptide, called pre-progastrin, which contains a signal sequence (underlined) that is cleaved, giving rise to progastrin, an 80-amino-acid polypeptide. Progastrin, in turn, is cleaved to generate a 34-amino-acid product, corresponding in sequence to residues 38-71 of progastrin, which is then extended at its carboxy terminus with a glycine residue, generating glycine-extended G34 ("G34-Gly"). A by-product of this cleavage is a 6-amino-acid peptide, called the C-terminal flanking peptide, or CTFP, which corresponds in sequence to residues 75-80 of progastrin. G34-Gly is then further cleaved to generate a 17-residue polypeptide corresponding in sequence to residues 55-71 of progastrin and referred to as G17-Gly. Removal of the C-terminal glycines of G34-Gly and G17-Gly, followed by C-terminal amidation, yields G34 and G17, respectively, both of which are C-terminal amidated.

As used herein, an antibody is "highly specific for" hPG or "highly specifically binds" hPG if it binds to full-length progastrin but does not bind at all to CTFP, to amidated gastrin, or to glycine-extended gastrin, and is "specific for" hPG or "specifically binds" hPG if it exhibits at least about 5-fold greater binding of hPG than CTFP and the other products of the gastrin gene, as measured in standard binding assays. A specific ELISA assay that can be used to assess the specificity of a particular anti-hPG antibody is provided in Example 2.

Such highly specific and/or specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The epitope bound by the anti-hPG antibodies is not critical. Useful anti-hPG antibodies may bind an N-terminal region of hPG, a C-terminal region of hPG, or a different region of hPG. Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076,454 to Singh) and a peptide corresponding to the last ten amino acids at the C-terminal end of hPG (see WO 07/135,542 to Hollande et al.) failed to generate monoclonal antibodies. As noted in the '329 and '041 applications, antigenic N-terminal and C-terminal sequences within the hPG sequence have been identified that can be used to generate nonoclonal antibodies that specifically bind hPG. Interestingly, the antigenic sequence need not be limited to regions of the hPG sequence that are unique to it. Peptide antigens having regions of sequence in common with other products of the gastrin gene, for example, G17, G34 and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDA-PLG (SEQ ID NO:25). Exemplary immunogens useful for obtaining N-terminal anti-hPG antibodies, as well as CDR and $V_H$ and $V_L$ sequences of N-terminal anti-hPG monoclonal antibodies obtained with these exemplary immunogens, are provided in TABLE 1A, below, and the Example sections:

TABLE 1A

N-Terminal Anti-hPG Monoclonal Antibodies

| Immunogen | Hybridoma (Deposit #) | MAb | Murine CDR Sequences | Murine $V_H$ and $V_L$ Sequences | Humanized $V_H$ and $V_L$ Sequences (projected) |
| --- | --- | --- | --- | --- | --- |
| N1 | 43B9G11 | MAb1 | | | |
| N1 | WE5H2G7 | MAb2 | | | |
| N2 | 6B5B11C10 | MAb3 | $V_H$ CDR 1.3<br>GYIFTSYW<br>(SEQ ID NO: 1)<br>$V_H$ CDR 2.3<br>FYPGNSDS<br>(SEQ ID NO: 2)<br>$V_H$ CDR 3.3<br>TRRDSPQY<br>(SEQ ID NO: 3) | m$V_H$.3<br>(SEQ ID NO: 12) | h$V_H$.3<br>(SEQ ID NO: 21) |
| | | | $V_L$ CDR 1.3<br>QSIVHSNGNTY<br>(SEQ ID NO: 4)<br>$V_L$ CDR 2.3<br>KVS<br>(SEQ ID NO: 5)<br>$V_L$ CDR 3.3<br>FQGSHVPFT<br>(SEQ ID NO: 6) | m$V_L$.3<br>(SEQ ID NO: 13) | h$V_L$.3<br>(SEQ ID NO: 22) |
| N2 | 20D2C3G2 | MAb4 | $V_H$ CDR 1.4<br>GYTFSSSW<br>(SEQ ID NO: 7)<br>$V_H$ CDR 2.4<br>FLPGSGST<br>(SEQ ID NO: 8)<br>$V_H$ CDR 3.4<br>ATDGNYDWFAY<br>(SEQ ID NO: 9) | m$V_H$.4<br>(SEQ ID NO: 14) | h$V_H$.4<br>(SEQ ID NO: 23) |

TABLE 1A-continued

N-Terminal Anti-hPG Monoclonal Antibodies

| Immunogen | Hybridoma (Deposit #) | MAb | Murine CDR Sequences | Murine $V_H$ and $V_L$ Sequences | Humanized $V_H$ and $V_L$ Sequences (projected) |
|---|---|---|---|---|---|
| | | | $V_L$ CDR 1.4 QSLVHSSGVTY (SEQ ID NO: 10) $V_L$ CDR 2.4 KVS (SEQ ID NO: 5) $V_L$ CDR 3.4 SQSTHVPPT (SEQ ID NO: 11) | $mV_L$.4 (SEQ ID NO: 15) | $hV_L$.4 (SEQ ID NO: 24) |
| N2 | 1E9A4A4 (I-4376) | MAb15 | | | |
| N2 | 1E9D9B6 | MAb16 | $V_H$ CDR 1.16 GYTFTSYY (SEQ ID NO: 39) $V_H$ CDR 2.16 INPSNGGT (SEQ ID NO: 43) $V_H$ CDR 3.16 TRGGYYPFDY (SEQ ID NO: 47) $V_L$ CDR 1.16 QSLLDSDGKTY (SEQ ID NO: 50) $V_L$ CDR 2.16 LVS (SEQ ID NO: 53) $V_L$ CDR 3.16 WQGTHSPYT (SEQ ID NO: 57) | $mV_H$.16 (SEQ ID NO: 61) $mV_L$.16 (SEQ ID NO: 65) | $hV_H$.16a (SEQ ID NO: 84) $hV_H$.16b (SEQ ID NO: 86) $hV_H$.16c (SEQ ID NO: 88) $hV_L$.16a (SEQ ID NO: 85) $hV_L$.16b (SEQ ID NO: 87) $hV_L$.16c (SEQ ID NO: 89) |
| N2 | 1C8D10F5 | MAb17 | | | |
| N2 | 1A7C3F11 | MAb18 | | | |
| N2 | 1B3B4F11 | MAb19 | $V_H$ CDR 1.19 GYSITSDYA (SEQ ID NO: 40) $V_H$ CDR 2.19 ISFSGYT (SEQ ID NO: 44) $V_H$ CDR 3.19 AREVNYGDSYHFDY (SEQ ID NO: 48) $V_L$ CDR 1.19 SQHRTYT (SEQ ID NO: 51) $V_L$ CDR 2.19 VKKDGSH (SEQ ID NO: 54) $V_L$ CDR 3.19 GVGDAIKGQSVFV (SEQ ID NO: 58) | $mV_H$.19 (SEQ ID NO: 62) $mV_L$.19 (SEQ ID NO: 66) | $hV_H$.19a (SEQ ID NO: 90) $hV_H$.19b (SEQ ID NO: 92) $hV_H$.19c (SEQ ID NO: 94) $hV_L$.19a (SEQ ID NO: 91) $hV_L$.19b (SEQ ID NO: 93) $hV_L$.19c (SEQ ID NO: 95) |
| N2 | 1C11F5E8 | MAb20 | | | |

Immunogen N1 = SWKPRSQQPDAPLG-Ahx-Cys-BSA, also represented as (SEQ ID NO: 25)-Ahx-Cys-BSA
Immunogen N2 = SWKPRSQQPDAPLG-Ahx-Cys-KLH, also represented as (SEQ ID NO: 25)-Ahx-Cys-KLH
In TABLE 1A, all amino acid sequences are represented using conventional N→C orientation. For each immunogen, the progastrin peptide was synthesized with a C-terminal linker of one aminohexanoic acid (Ahx) residue followed by a cysteine (Cys) residue, which was then conjugated to a either a bovine serum albumin ("BSA") or keyhole limpet hemocyanin ("KLH") carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYG-WMDFGRRSAEDEN (SEQ ID NO:27). Exemplary immunogens including this antigen useful for obtaining C-terminal anti-hPG antibodies, as well as CDR and $V_H$ and $V_L$ sequences of C-terminal anti-hPG monoclonal antibodies obtained with these exemplary immunogens, are provided in TABLE 1B, below, and the Examples section.

TABLE 1B

C-Terminal Anti-hPG Monoclonal Antibodies

| Immunogen | Hybridoma (Deposit #) | MAb | Murine CDR Sequences | Murine $V_H$ and $V_L$ Sequences | Humanized $V_H$ and $V_L$ Sequences (projected) |
|---|---|---|---|---|---|
| C1 | 1B4A11D11 (I-4371) | MAb5 | | | |
| C1 | 1B6A11F2 (I-4372) | MAb6 | | | |
| C1 | 1B11E4B11 (I-4373) | MAb7 | | | |
| C1 | 1C10D3B9 | MAb8 | $V_H$ CDR 1.8 GFTFTTYA (SEQ ID NO: 37) $V_H$ CDR 2.8 ISSGGTYT (SEQ ID NO: 41) $V_H$ CDR 3.8 ATQGNYSLDF (SEQ ID NO: 45) $V_L$ CDR 1.8 KSLRHTKGITF (SEQ ID NO: 49) $V_L$ CDR 2.8 QMS (SEQ ID NO: 52) $V_L$ CDR 3.8 AQNLELPLT (SEQ ID NO: 55) | $mV_H.8$ (SEQ ID NO: 59) $mV_L.8$ (SEQ ID NO: 63) | $hV_H.8a$ (SEQ ID NO: 75) $hV_H.8b$ (SEQ ID NO: 77) $hV_H.8c$ (SEQ ID NO: 79) $hV_L.8a$ (SEQ ID NO: 76) $hV_L.8b$ (SEQ ID NO: 78) $hV_L.8c$ (SEQ ID NO: 76) |
| C1 | 1D8F5B3 | MAb9 | | | |
| C1 | 1E1C7B4 | MAb10 | | | |
| C1 | 2B4C8C8 (I-4374) | MAb11 | | | |
| C1 | 2B11E6G4 (I-4375) | MAb12 | | | |
| C1 | 2C6C3C7 | MAb13 | $V_H$ CDR 1.13 GFIFSSYG (SEQ ID NO: 38) $V_H$ CDR 2.13 INTFGDRT (SEQ ID NO: 42) $V_H$ CDR 3.13 ARGTGTY (SEQ ID NO: 46) $V_L$ CDR 1.13 QSLLDSDGKTY (SEQ ID NO: 50) $V_L$ CDR 2.13 LVS (SEQ ID NO: 53) $V_L$ CDR 3.13 WQGTHFPQT (SEQ ID NO: 56) | $mV_H.13$ (SEQ ID NO: 60) $mV_L.13$ (SEQ ID NO: 64) | $hV_H.13a$ (SEQ ID NO: 80) $hV_H.13b$ (SEQ ID NO: 82) $hV_L.13a$ (SEQ ID NO: 81) $hV_L.13b$ (SEQ ID NO: 83) |
| C1 | 2H9F4B7 | MAb14 | | | |
| C2 | 1F11F5E10 | MAb21 | | | |
| C2 | 1F11F5G9 | MAb22 | | | |
| C2 | 1A11F2C9 | MAb23 | | | |

Immunogen C1 = KLH-Cys-Ahx-Ahx-QGPWLEEEEEAYGWMDFGRRSAEDEN, also represented as KLH-Cys-Ahx-Ahx-(SEQ ID NO: 27)
Immunogen C2 = DT-Cys-Ahx-Ahx-QGPWLEEEEEAYGWMDFGRRSAEDEN, also represented as DT-Cys-Ahx-Ahx-(SEQ ID NO: 27)
In TABLE 1B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in TABLES 1A and 1B were mapped using the SPOT technique and alanine scanning, as described in Laune et al., 2002, J. Immunol. Methods 267:53-70 and Laune, 1997, J. Biol. Chem. 272:30937-30944, respectively (see also, Example 6 of the '329 application).

In the SPOT technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in TABLE 2A below.

TABLE 2A

| MAb # | PG peptide antigen: SWKPRSQQPDAPLG | SEQ ID NO |
|---|---|---|
| MAb2 | WKPRSQQPDAPLG | 32 |
| MAb4 | WKPRSQQPDAPLG | 32 |
| MAb1 | PDAPLG | 29 |
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbs5-7, 9-12, 14 and 21-23, epitopes comprise at least the following sequences: FGRR (SEQ ID NO:33), MDFGR (SEQ ID NO:34), AEDEN (SEQ ID NO:35), and GWMDFGRR (SEQ ID NO:36), as shown in TABLE 2B, below.

TABLE 2B

| MAb # | PG peptide antigen: QGPWLEEEEEAYGWMDFGRRSAEDEN | SEQ ID NO |
|---|---|---|
| MAb14 | GWMDFGRR | 36 |
| MAb11 | MDFGR | 34 |
| MAb5 | FGRR | 33 |
| MAb6 | FGRR | 33 |
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in TABLES 1A & 1B can be identified in competitive binding assays with exemplary MAbs 1-23, or with other reference antibodies that bind N- or C-terminal epitopes, as will be described in more detail in a later section.

As also reported in the '329 and '041 applications, not all anti-hPG antibodies, even those that exhibit a high degree of specificity and affinity for hPG, may neutralize the biological activity of hPG. For example, although anti-hPG MAb14 binds hPG with a $K_D$ of about 6 pM, it did not inhibit the growth of colorectal cancer cells in an in vitro assay, whereas other anti-hPG monoclonal antibodies exhibited significant inhibitory activity (see, e.g., Example 7 of the '329 application). While both non-neutralizing and neutralizing antibodies that specifically bind hPG are useful for the various diagnostic and monitoring methods described herein, anti-hPG antibodies useful for therapeutic methods should exhibit neutralizing activity.

As used herein, a "neutralizing anti-hPG antibody" is an anti-hPG antibody that yields a statistically significant reduction in the number of live BxPC-3 cells in a test sample treated with the anti-hPG antibody as compared to a control sample treated with a non-specific antibody. A specific assay for assessing the ability of any particular anti-hPG antibody to neutralize hPG is described in Example 3. Those anti-hPG antibodies that exhibit at least about a 50% reduction in the number of live cells in this assay are believed to be especially useful in treating pancreatic cancer, although anti-hPG antibodies exhibiting lower levels of neutralizing activity, for example, a statistically significant reduction of 40%, 30%, 20%, 15%, or even 10%, in the number of live cells in this assay are expected to provide therapeutic benefits.

Accordingly, in some embodiments, for example therapeutic embodiments, useful anti-hPG antibodies are neutralizing. As disclosed in the '329 and '041 applications, the ability of an anti-hPG monoclonal antibody is not epitope-dependent, as both N-terminal and C-terminal anti-hPG monoclonal antibodies exhibited neutralizing activity in assays with pancreatic cancer cells. Thus, in some specific embodiments, the neutralizing anti-hPG antibodies are N-terminal neutralizing anti-hPG antibodies. In other embodiments, the neutralizing anti-hPG antibodies are C-terminal neutralizing anti-hPG antibodies.

The affinity of any specific anti-hPG antibody is not critical. However, for some uses, antibodies exhibiting affinities of at least about 1 µM may be preferred. For therapeutic uses, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, or even greater, may be desirable. The measured affinities of the anti-hPG monoclonal antibodies identified in TABLES 1A & 1B range from $10^{-6}$ to $10^{-12}$ M, as noted in TABLE 3, below:

TABLE 3

| MAb# | Affinity (measured $K_D$) |
|---|---|
| MAb1 | 2.5 µM (2.5 × $10^{-6}$M) |
| MAb2 | 185 nM (1.85 × $10^{-7}$M) |
| MAb3 | 6.4 nM (6.4 × $10^{-9}$M) |
| MAb4 | 3.5 nM (3.5 × $10^{-9}$M) |
| MAb5 | 13 pM (1.30 × $10^{-11}$M) |
| MAb6 | 0.6 nM (6.38 × $10^{-10}$M) |
| MAb7 | 58 pM (5.84 × $10^{-11}$M) |
| MAb8 | 0.1 nM (1.08 × $10^{-10}$M) |
| MAb10 | 3.6 nM (3.62 × $10^{-9}$M) |
| MAb11 | 0.3 nM (3.12 × $10^{-10}$M) |
| MAb12 | 0.4 nM (4.43 × $10^{-10}$M) |
| MAb13 | 0.6 nM (6.12 × $10^{-10}$M) |
| MAb14 | 6.8 pM (6.86 × $10^{-12}$M) |
| MAb15 | 0.2 nM (2.11 × $10^{-10}$M) |
| MAb16 | 0.2 nM (2.78 × $10^{-10}$M) |
| MAb17 | 8.3 nM (8.29 × $10^{-9}$M) |
| MAb18 | 1.2 nM (1.24 × $10^{-9}$M) |
| MAb19 | 0.7 nM (7.79 × $10^{-10}$M) |
| MAb20 | 0.2 nM (2.47 × $10^{-10}$M) |
| MAb21 | 3.9 nM (3.90 × $10^{-9}$M) |
| MAb22 | 5 nM (4.94 × $10^{-9}$M) |
| MAb23 | 0.4 µM (3.99 × $10^{-7}$M) |

An anti-PG monoclonal antibody having an affinity especially suited for a particular desired application can be readily selected from amongst these, or generated or designed using the various immunogens, complementarity determining region (CDR) sequences, variable heavy ($V_H$) and variable light ($V_L$) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 4.

As noted in TABLES 1A & 1B, several N-terminal and C-terminal monoclonal anti-hPG antibodies have been identified. All of these antibodies are specific for hPG, and, with the exception of MAb14, all exhibited neutralizing activity in tests with colorectal cancer cells. All of the antibodies tested with pancreatic cancer cells (MAbs 8, 13, 16 and 19) exhibited neutralizing activity. Several of the hybridomas useful for obtaining the antibodies were deposited on Oct. 6, 2010 with the Collection Nationale de Cultures de Microorganisms (CNCM) in accordance with the Treaty of Budapest. The designated names of the hybridomas producing anti-hPG MAbs1-23 and the depository registration numbers of those hybridomas deposited are provided in TABLES 1A & 1B. In addition, for several of the antibodies, the amino acid sequences of their variable heavy chains ($V_H$), variable light chains ($V_L$), $V_L$ complementarity determining regions (CDRs) and $V_H$ CDRs have been determined. These amino acid sequences, and the shorthand nomenclature used to reference them throughout the disclosure, are also provided in TABLES 1A & 1B. Briefly, murine heavy and light chain variable domains are referred to herein as $mV_H$ and $mV_L$ followed by the number of the corresponding monoclonal antibody, for example $mV_H.3$ and $mV_L.3$ for the variable light and variable heavy chains of anti-hPG MAb3, respectively. Similarly, human heavy and light chain variable domains are referred to herein as $hV_H$ and $hV_L$ followed by the number of the corresponding monoclonal antibody. The three variable heavy chain CDRs and three variable light chain CDRs are referred to as $V_H$ CDR 1, 2, or 3, and $V_L$ CDR 1, 2, or 3, respectively, followed by the number of the specific anti-hPG monoclonal antibody. For example, $V_H$ CDR 1 of MAb3 is denoted $V_H$ CDR 1.3 and $V_L$ CDR 1 of MAb3 is denoted $V_L$ CDR 1.3. $V_H$ CDR 2 of MAb3 is denoted $V_H$ CDR 2.3, and $V_L$ CDR 2 of MAb3 is denoted $V_L$ CDR 2.3.

It is expected that corresponding CDRs and/or $V_H$ and $V_L$ chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its $V_L$ chain, various combinations of the $V_L$ CDRs of these two antibodies, and/or in its $V_H$ chain various combinations of the $V_H$ CDRs of these two antibodies. As a specific non-limiting example to illustrate the various combinations possible, such an antibody could include in its $V_L$ chain, CDRs 1 and 2 of MAb5 ($V_L$ CDR 1.5 and $V_L$ CDR 2.5, respectively) and CDR 3 of MAb6 ($V_L$ CDR 3.6), and in its $V_H$ chain, CDR 1 of MAb6 ($V_H$ CDR 1.6) and CDRs 2 and 3 of MAb5 ($V_H$ CDR 2.5 and $V_H$ CDR 3.5, respectively). Amino acid sequences of CDRs of antibodies (also known as hypervariable regions) produced by hybridomas that have been deposited can be obtained using conventional means.

As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The anti-PG antibodies described herein may contain modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., 1987, *Sequences of Proteins of Immunological Interest*, National Institute of Health, Bethesda, Md.). As used herein, numbering of immunoglobulin amino acid residues is done according to the immunoglobulin amino acid residue numbering system of Kabat et al., unless otherwise indicated.

With reference to TABLE 1A, specific embodiments of N-terminal anti-hPG antibodies useful in the methods and kits described herein include, but are not limited to, the following:

(a) antibodies having $V_L$ CDRs that correspond in sequence to the $V_L$ CDRs of MAb1, MAb2, MAb3, MAb4, MAb15, MAb16, MAb17, MAb18, MAb19 or MAb20, and $V_H$ CDRs that correspond in sequence to the $V_H$ CDRs of MAb1, MAb2, MAb3, MAb4, MAb15, MAb16, MAb17, MAb18, MAb19 or MAb20;

(b) antibodies having $V_L$ CDRs and $V_H$ CDRs that correspond in sequence to the $V_L$ and $V_H$ CDRs of MAb1, MAb2, MAb3, MAb4, MAb15, MAb16, MAb17, MAb18, MAb19 or MAb20;

(c) antibodies in which:

(i) $V_L$ CDR 1 is selected from QSIVHSNGNTY ("$V_L$ CDR 1.3"; SEQ ID NO:4), QSLVHSSGVTY ("$V_L$ CDR 1.4"; SEQ ID NO:10), QSLLDSDGKTY ("$V_L$ CDR 1.16"; SEQ ID NO:50), and SQHRTYT ("V$_L$ CDR 1.19"; SEQ ID NO:51);

(ii) V$_L$ CDR 2 is selected from KVS ("V$_L$ CDR 2.3" or "V$_L$ CDR 2.4"; SEQ ID NO:5), LVS ("V$_L$ CDR 2.16"; SEQ ID NO:53), and VKKDGSH ("V$_L$ CDR 2.19"; SEQ ID NO:54);

(iii) V$_L$ CDR 3 is selected from FQGSHVPFT ("V$_L$ CDR\ 3.3"; SEQ ID NO:6), SQSTHVPPT ("V$_L$ CDR 3.4"; SEQ ID NO:11), WQGTHSPYT ("V$_L$ CDR 3.16"; SEQ ID NO:57), and GVGDAIKGQSVFV ("V$_L$ CDR 3.19"; SEQ ID NO:58);

(iv) V$_H$ CDR 1 is selected from GYIFTSYW ("V$_H$ CDR 1.3"; SEQ ID NO:1), GYTFSSSW ("V$_H$ CDR 1.4"; SEQ ID NO:7), GYTFTSYY ("V$_H$ CDR 1.16"; SEQ ID NO:39), and GYSITSDYA ("V$_H$ CDR 1.19"; SEQ ID NO:40);

(v) V$_H$ CDR 2 is selected from FYPGNSDS ("V$_H$ CDR 2.3"; SEQ ID NO:2), FLPGSGST ("V$_H$ CDR 2.4"; SEQ ID NO:8), INPSNGGT ("V$_H$ CDR 2.16"; SEQ ID NO:43), and ISFSGYT ("V$_H$ CDR 2.19"; SEQ ID NO:44); and (vi) V$_H$ CDR 3 is selected from TRRDSPQY ("V$_H$ CDR 3.3"; SEQ ID NO:3), ATDGNYDWFAY ("V$_H$ CDR 3.4" SEQ ID NO:9), TRGGYYPFDY ("V$_H$ CDR 3.16"; SEQ ID NO:47), and AREVNYGDSYHFDY ("V$_H$ CDR 3.19"; SEQ ID NO:48);

(d) antibodies having a V$_L$ that corresponds in sequence to the V$_L$ of MAb1, MAb2, MAb3, MAb4, MAb15, MAb16, MAb17, MAb18, MAb19 or MAb20 and a V$_H$ that corresponds in sequence to the V$_H$ of MAb1, MAb2, MAb3, MAb4, MAb15, MAb16, MAb17, MAb18, MAb19 or MAb20; and (e) antibodies having a V$_L$ and a V$_H$ that correspond in sequence to the V$_L$ and V$_H$ of MAb1, MAb2, MAb3, MAb4, MAb15, MAb16, MAb17, MAb18, MAb19 or MAb20.

With reference to TABLE 1B, specific embodiments of C-terminal anti-hPG antibodies useful in the methods and kits described herein include, but are not limited to, the following:

(f) antibodies having V$_L$ CDRs that correspond in sequence to the V$_L$ CDRs of MAb5, MAb6, MAb7, MAb8, MAb9, MAb10, MAb11, MAb12, MAb13, MAb14, MAb21, MAb22 or MAb23 and V$_H$ CDRs that correspond in sequence to the V$_H$ CDRs of MAb5, MAb6, MAb7, MAb8, MAb9, MAb10, MAb11, MAb12, MAb13, MAb14, MAb21, MAb22 or MAb23;

(g) antibodies having V$_L$ CDRs and V$_H$ CDRs that correspond in sequence to the V$_L$ and V$_H$ CDRs of MAb5, MAb6, MAb7, MAb8, MAb9, MAb10, MAb11, MAb12, MAb13, MAb14, MAb21, MAb22 or MAb23;

(h) antibodies in which:

(i) V$_L$ CDR 1 is selected from KSLRHTKGITF ("V$_L$ CDR 1.8"; SEQ ID NO:49) and QSLLDSDGKTY ("V$_L$ CDR 1.13"; SEQ ID NO:50);

(ii) V$_L$ CDR 2 is selected from QMS ("V$_L$ CDR 2.8"; SEQ ID NO:52) and LVS ("V$_L$ CDR 2.13"; SEQ ID NO:53);

(iii) V$_L$ CDR 3 is selected from AQNLELPLT ("V$_L$ CDR 3.8"; SEQ ID NO:55) and WQGTHFPQT ("V$_L$ CDR 3.13"; SEQ ID NO:56);

(iv) V$_H$ CDR 1 is selected from GFTFTTYA ("V$_H$ CDR 1.8"; SEQ ID NO:37) and GFIFSSYG ("V$_H$ CDR 1.13"; SEQ ID NO:38);

(v) V$_H$ CDR 2 is selected from ISSGGTYT ("V$_H$ CDR 2.8"; SEQ ID NO:41) and INTFGDRT ("V$_H$ CDR 2.13"; SEQ ID NO:42); and (vi) V$_H$ CDR 3 is selected from ATQGNYSLDF ("V$_H$ CDR 3.8"; SEQ ID NO:45) and ARGTGTY ("V$_H$ CDR 3.13"; SEQ ID NO:46);

(i) antibodies having a V$_L$ that corresponds in sequence to the V$_L$ of MAb5, MAb6, MAb7, MAb8, MAb9, MAb10, MAb11, MAb12, MAb13, MAb14, MAb21, MAb22 or MAb23 and a V$_H$ that corresponds in sequence to the V$_H$ of MAb5, MAb6, MAb7, MAb8, MAb9, MAb10, MAb11, MAb12, MAb13, MAb14, MAb21, MAb22 or MAb23; and (j) antibodies having a V$_L$ and a V$_H$ that correspond in sequence to the V$_L$ and V$_H$ that correspond in sequence to the V$_L$ and V$_H$ of MAb5, MAb6, MAb7, MAb8, MAb9, MAb10, MAb11, MAb12, MAb13, MAb14, MAb21, MAb22 or MAb23.

As will be appreciated by skilled artisans, anti-hPG antibodies useful in the diagnostic methods can be of any origin, including, for example, mammalian (e.g., human, primate, rodent, goat or rabbit), non-mammalian, or chimeric in nature (derived from more than one species of origin). Antibodies suitable for therapeutic uses in animals, including humans, are preferably derived from the same species intended to be treated, or have been modified or designed to be non-immunogenic or have reduced immunogenicity in the animal being treated. A specific class of anti-hPG antibodies useful for therapeutic uses in humans is the class of humanized antibodies, discussed in more detail, below. Anti-hPG antibodies useful in the methods and kits described herein can also be of, or derived from, any isotype, including, for example, IgA (e.g., IgA1 or IgA2), IgD, IgE, IgG (e.g., IgG1, IgG2, IgG3 or IgG4) or IgM. Anti-hPG antibodies designed for therapeutic uses are preferably of the IgG isotype.

In some embodiments, anti-hPG antibodies useful for therapeutic methods described herein are humanized. In general, humanized antibodies comprise substantially all of at least one, and typically two, variable domains, in which all or substantially all of the CDR regions correspond to those of a non-human immunoglobulin and all or substantially all of the framework regions are those of a human immunoglobulin consensus sequence, and can be referred to as "CDR-grafted." The humanized antibody can also comprise at least a portion of an immunoglobulin constant region (Fc), typically that of a human immunoglobulin consensus sequence. Methods for humanizing antibodies, including methods for designing humanized antibodies, are well-known in the art. See, e.g., Lefranc et al., 2003, Dev. Comp. Immunol. 27:55-77; Lefranc et al., 2009, Nucl. Acids Res. 37:D1006-1012; Lefranc, 2008, Mol. Biotechnol. 40: 101-111; Riechmann et al., 1988, Nature 332:323-7; U.S. Pat. Nos. 5,530,101, 5,585,089, 5,693,761, 5,693,762 and 6,180, 370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814; Roguska et al., 1994, Proc. Natl. Acad. Sci. 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in TABLE 1A and the various C-terminal anti-hPG monoclonal antibodies provided in TABLE 1B, can be obtained using these well-known methods. Projected sequences for humanized V$_L$ and V$_H$ chains of selected anti-hPG antibodies are provided in TABLES 1A and 1B. Specific examples of humanized antibodies include antibodies comprising:

(k) any three $V_L$ CDRs and any three $V_H$ CDRs disclosed herein;

(l) a heavy chain variable region comprising an amino acid sequence corresponding to SEQ ID NO:21 and a light chain variable region comprising an amino acid sequence corresponding to SEQ ID NO:22;

(m) a heavy chain variable region comprising an amino acid sequence corresponding to SEQ ID NO:23 and a light chain variable region comprising an amino acid sequence corresponding to SEQ ID NO:24;

(n) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(o) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(p) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (q) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 5.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming an hPG: labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 5.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 5, by at least 50%, at a test antibody concentration in the range of 0.01-100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable.

Skilled artisans will appreciate that is some contexts, for example, diagnostic and monitoring contexts, it may be desirable to label the anti-PG antibodies. Such labels are useful for detection and quantification. Suitable labels are well known in the art, and can be "direct" in that they are directly observable or detectable (for example, fluorophores or radioisotopes) or "indirect" in that they interact with something else that produces and observable or detectable signal (for example, an enzyme that acts on a substrate to produce a detectable signal, or a binding molecule such as biotin that binds a labeled, streptavidin molecule). Numerous labeling systems, as well as means for labeling antibodies with them, are known in the art, and are contemplated for use herein.

Although the various anti-hPG antibodies useful in the methods described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')2, Fab, Fv, vIgG, scFv fragments and surrobodies. Unless specified otherwise, the term "antibody" as used herein is intended to include all forms of antibodies and "antibody-like" surrogate molecules, including single chain antibodies, surrobodies and binding fragments. Antibodies having structures typical of naturally occurring antibodies are referred to herein as "native antibodies."

7.10 Methods of Producing Anti-PG Antibodies

Anti-PG antibodies useful in the methods described herein may be obtained using standard, well-known methods. To express anti-PG antibodies useful in the methods described herein, DNAs encoding partial or full-length light and heavy chains are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-PG antibody light or heavy chain sequences, the expression vector can already carry antibody constant region sequences. For example, one approach to converting the anti-PG antibody $V_H$ and $V_L$ sequences to full-length antibody genes is to insert them into expression vectors already encoding heavy chain constant and light chain constant regions, respectively, such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, *Gene Expression Technology: Methods in Enzymology* 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR-host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies described herein in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR-CHO cells, described in Urlaub & Chasin, 1980, Proc. Natl. Acad. Sci. USA 77:4216-4220, used with a DHFR selectable marker, e.g., as described in Kaufman & Sharp, 1982, Mol. Biol. 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as $F_{ab}$ fragments or $scF_v$ molecules. It is understood that variations on the above procedure are within the scope of the present disclosure. For example, it can be desirable to transfect a host cell with DNA encoding either the light chain or the heavy chain (but not both) of an anti-PG antibody described herein.

Recombinant DNA technology can also be used to remove some or all of the DNA encoding either or both of the light and heavy chains that is not necessary for binding to PG. The molecules expressed from such truncated DNA molecules are also useful in the methods described herein.

For recombinant expression of an anti-PG antibody, the host cell can be co-transfected with two expression vectors, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Anti-PG antibodies can also be produced by chemical synthesis (e.g., by the methods described in *Solid Phase Peptide Synthesis*, 2nd ed., 1984 The Pierce Chemical Co., Rockford, Ill.). Variant antibodies can also be generated using a cell-free platform ((see, e.g., Chu et al., 2001, Biochemia No. 2 (Roche Molecular Biologicals)).

Once an anti-PG antibody has been produced by recombinant expression or synthetic means, it can be purified by any method known in the art for purification of an immunoglobulin molecule, for example, by chromatography (e.g., ion exchange, affinity, particularly by affinity for PG after Protein A or Protein G selection, and sizing column chromatography), centrifugation, differential solubility, or by any other standard technique for the purification of proteins. Further, the anti-PG antibodies or binding fragments thereof can be fused to heterologous polypeptide sequences described herein or otherwise known in the art to facilitate purification.

8. EXAMPLES 8.1 Example 1: Quantification of Plasma or Serum PG Levels

Plasma and/or serum levels of PG can be conveniently determined using the following assay. 96-well microtiter plates are coated with between 0.5 and 10 μg/mL of a C-terminal anti-hPG antibody, for example, a rabbit C-terminal anti-hPG polyclonal antibody, or a C-terminal anti-hPG antibody described herein, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 μg/mL of an N-terminal anti-hPG antibody, for example, a polyclonal N-terminal anti-hPG antibody or an N-terminal monoclonal anti-hPG antibody as described herein, coupled to horseradish peroxidase (HRP) ((see, Nakane et al., 1974, J. Histochem. Cytochem. 22(12):1084-1091)) for 30 minutes at 21° C. Plates are then washed three times in PBS-Tween (0.05%) and HRP substrate is added for 15 minutes at 21° C. The reaction is stopped by added 100 μL of 0.5M sulfuric acid and an optical density measurement is taken at 405 nm. Test sample hPG levels are determined by comparison to a standard curve constructed from the measurements derived from the hPG reference standard.

8.2 Example 2: ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 μL blocking solution (PBS, 0.1% Tween-20, 0.1% Bovine Serum Albumin or casein hydrolysate) per well. After blocking, the wells are washed three times and the antibody to be assayed (test antibody) is added. 100 μL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3×100 μL wash solution, as noted above), with blocking solution containing a secondary antibody, a goat anti-mouse IgG (Fc) antibody coupled to horseradish peroxidase. After a 1-hour incubation with secondary antibody, 100 μL of substrate solution (e.g. Fast OPD, or O-Phenylenediamine dihydrochloride, available from Sigma-Aldrich Co., prepared according to manufacturer's directions) is added to each well and incubated in the dark for 20 minutes at 22° C. The reaction is stopped by adding 50 μL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as specific for PG if the measured O.D. is between 0.2 and 1.5 for hPG and there is no statistically significant signal above background with CTFP or any of the other gastrin-gene derived peptides, where the background is the average signal from control wells containing only PBS.

8.3 Example 3; Assay for Assessing Neutralizing Activity of Anti-hPG Antibodies

A specific test for assessing whether a specific anti-hPG antibody is neutralizing can be performed as follows. BxPC-3 pancreatic cancer cells are seeded in 6 wells of a 6-well plate, at approximately 150,000 cells per well. Cells are then treated at 12-hour intervals for 48 hours with the test anti-hPG antibody or a control antibody, at antibody concentrations of about 5 μg/mL. A test antibody is defined as neutralizing in the assay, if the number of cells treated with the test antibody shows a statistically significant reduction of at least 10% in the number of surviving cells compared to the number of cells treated with a control, non-specific antibody, using a two-tailed Mann-Whitney test (with differences considered as significant when $p<0.05$). Total cell numbers are corrected for the number of cells at the start of the treatment period, referred to as $T_0$.

8.4 Example 4: Assay for Assessing Affinity of an Anti-hPG Antibody

Affinity constants of anti-hPG antibodies can be measured using the Proteon Technique (BioRad), according to Nahshol et al., 2008, Analytical Biochemistry 383:52-60, hereby incorporated by reference in its entirety. Briefly, for murine anti-PG antibodies, an anti-mouse IgG antibody (50 μg/ml) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 μg/ml). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

8.5 Example 5: Assay for Assessing Competitive Binding with a Reference Anti-hPG Antibody A specific assay for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N- or C-terminal region of hPG that differs from the epitope recognized by the biotinylated reference anti-hPG antibody), at a concentration to be chosen within the range of 1-10 μg/ml, overnight at 4° C. (0.1 to 1 μg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/ml steptavidin-HRP for 1 hr at 22° C., followed by incubation with a fluorogenic substrate for horseradish peroxidase for 1 hr at 22° C., and then quantifying the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody.

In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$, which is calculated according to the following formula:

$$K_i = IC_{50}/[1+(\text{reference anti-hPG Ab concentration}/K_D^{reference\ anti-hPG\ Ab})]$$

where "$IC_{50}$" is the concentration of test antibody that yields a 50% reduction in binding of the reference antibody and $K_D^{reference\ anti-hPG\ Ab}$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

8.6 Example 6: Plasma or Serum Progastrin Concentrations in Patients Diagnosed with Primary and Metastatic Pancreatic Cancer This example demonstrates that patients diagnosed with either primary or metastatic pancreatic cancer have elected plasma or serum levels of progastrin.

8.6.1 Methods

Plasma or serum progastrin concentrations were measured in healthy individuals, as a control, and in patients diagnosed with pancreatic, stomach, esophageal, ovarian or breast cancer. Healthy control samples (n=104) were obtained from a blood bank. Of the patients involved in the analysis, 25/32 pancreatic cancer patients had metastatic disease, ten of whom had their primary tumors removed.

Quantification of plasma or serum progastrin levels was performed using a progastrin-specific sandwich ELISA technique similar to the one described prophetically below.

The wells of Nunc MaxiSORP 96-well plates are coated with a first progastrin-specific antibody as follows. Anti-progastrin polyclonal antibodies specific for the carboxy-terminal region of progastrin are diluted to a concentration of 3 µg/ml in a solution of 50 mM, pH 9.6 sodium carbonate/bicarbonate buffer in MilliQ water. A total of 100 µl of the antibody solution is then added to each well of the 96-well plates, and incubated overnight at 4° C. After binding, the antibody solution is removed from the wells, which are then washed three times with 100 µl wash buffer (1×PBS/0.1% Tween-20). A total of 100 µl blocking buffer (1×PBS/0.1% Tween-20/0.1% BSA) is then added to each well and incubated for 2 hours at 22° C. Blocking buffer is then removed and the wells washed three times with wash buffer. Plasma or serum samples isolated from patients is then added to the wells in a volume of 100 µl in a dilution series, typically 1:1, 1:2, 1:5 and 1:10 dilutions, and is then incubated for 2 hours at 22° C. Plasma or serum samples are analyzed in duplicate.

Assays also include two standard curves. The first standard curve is prepared using dilutions of recombinant progastrin to a final amount of 1 ng, 0.5 ng, 0.25 ng, 0.1 ng, 0.05 ng, 0.01 ng, and 0 ng per well. The second standard curve, which serves as a negative control, is prepared from progastrin-negative human serum diluted in blocking buffer at the same dilutions as the test samples, i.e., 1:1, 1:2, 1:5 and 1:10. Alternatively, when plasma samples are being assayed, the second standard curve, which serves as a negative control, is prepared from progastrin-negative human plasma diluted in blocking buffer at the same dilutions as the test samples, i.e., 1:1, 1:2, 1:5 and 1:10.

After incubation with the plasma or serum samples is complete, the well contents are removed and the wells are washed three times with wash buffer, 100 µl/well, after which progastrin bound to the first antibody is detected using a second antibody specific for progastrin, as follows.

Biotin-coupled anti-progastrin polyclonal or monoclonal antibodies specific for the amino-terminal region of progastrin are diluted in blocking buffer to a concentration of 0.1 to 10 µg/ml, depending on the antibody. A total of 100 µl of the antibody solution is then added to each well, and incubated for 1 hour at 22° C.

After secondary antibody binding is complete, the plates are washed three times with wash buffer, 100 µl/well, after which 100 µl of a solution of streptavidin-HRP (25 ng/ml in blocking buffer) is added to each well and incubated for 1 hour at 22° C. After incubation with the streptavidin-HRP solution is complete, the plates are washed three times with wash buffer, 100 µl/well. Thereafter, 100 µl of chemiluminescent substrate prepared using a Pierce SuperSignal ELISA Femto Maximum Sensitivity Chemiluminescent Substrate kit, is added per well, incubated for 5 min at room temperature in the dark, and then read on a luminometer.

Based on the luminometer readings, linear regression analysis is used to derive the equation of the lines corresponding to the standard curve data. Using this equation, the concentration of progastrin in the various patient samples is then calculated.

8.6.2 Results

The box plots in FIG. 4 shows the $25^{th}$ percentile, median, and $75^{th}$ percentile plasma or serum progastrin concentrations of cancer patients assayed, compared to healthy controls. The whiskers indicate the 5th and 95th percentiles of plasma or serum progastrin concentrations. This data demonstrates that patient populations comprising patients with primary and metastatic pancreatic cancer had elevated levels of progastrin in their plasma or serum compared to healthy individuals.

8.7 Example 7: Expression of Gastrin Gene in Primary and Metastatic Pancreatic Cancer Cell Lines This example shows that the GAST gene is expressed in primary and metastatic pancreatic cancer cell lines.

8.7.1 Method

Cells tested were from the primary pancreatic cancer cell lines BxPC-3 and MIA PaCa-2, and the metastatic pancreatic cancer cell lines Capan 1 and SU.86.86. After a period of growth, cells were re-suspended and lysed, and total mRNA was extracted using QIAGEN Rneasy Mini-kit according to the manufacturer's protocol. RNA was reverse transcribed using Superscript II RT (Invitrogen) in the presence of Oligo(dT)15 primer (Roche Applied Science). Real-time PCR was performed using the Quantifast SYBR Green PCR kit (Qiagen) and the Eppendorf Mastercycler ep realplex (Eppendorf). Primers for GAST and GAPDH gene amplification were obtained from Sigma Life Science. Each PCR amplification was performed in triplicate wells using the following conditions: 5 min at 95° C., followed by a total of 45 two-temperature cycles (10 sec at 95° C. and 30 sec at 60° C.).

8.7.2 Results

The relative levels of gastrin mRNA expressed in the different cell lines are reported in FIG. 56. Levels were normalized relative to the amount of GAST mRNA expressed in the LS174T colorectal cancer cell line, which served as a positive control, and data are expressed relative to expression levels in the LS174T CRC cell line. All pancreatic cancer cell lines tested express mRNA for the progastrin-encoding gene (GAST).

8.8 Example 8: Secretion of Progastrin by Pancreatic Cancer Cell Lines

This example demonstrates that pancreatic cancer cell lines secrete progastrin.

8.8.1 Method

Secretion of progastrin was quantified using a sandwich ELISA technique in conditioned medium obtained from pancreatic cells grown in 2D culture, using the following protocol. Cells were grown in a 75 cm$^2$ flask until they reached 60% confluence. Medium was then removed and cells were rinsed once with PBS. Cells were then grown in 20 ml of M11 medium (without phenol red) for 48 hr. Medium was then collected, centrifuged at 1,000 g for 5 min to remove cell debris, and frozen at −80° C. Cells were then trypsinized and counted.

To measure secreted progastrin, the frozen medium was slowly thawed on ice, and then concentrated 40-fold to a volume of 500 μl using protein concentrators (Icon Pierce) by centrifugation at 2,500 g for 45 minutes. Progastrin concentration was then measured using a sandwich ELISA technique.

8.8.2 Results

The concentrations of progastrin in medium conditioned by the pancreatic cancer cell lines is reported in FIG. 6. Data are expressed as progastrin concentration in pM, per million cells per 48 hours of growth.

8.9 Example 9: Effect of Anti-hPG Monoclonal Antibodies on Growth of Capan 1 Metastatic Pancreatic Cancer Cells in Culture This example demonstrates that anti-hPG antibodies inhibit the proliferation of metastatic pancreatic tumor cells.

8.9.1 Methods

Capan 1 cells were seeded into 6-well plates (50,000 cells/well) and grown in DMEM containing 20% fetal calf serum for 8 hours. Cells were serum-starved overnight, and starting at 24 hours after seeding (time T0), cells were treated every 12 hours for 48 hours, in the presence of 0.5% PanexinH, with 1 μg/ml of control monoclonal antibody (mouse anti-human IgG1, Calbiochem Ref #411451) or with 1 μg/ml anti-hPG MAb3 as indicated. The technician was blinded as to the contents of the treatment solutions.

8.9.2 Results

The results, shown in FIG. 7, were calculated as the average number of cells per well at the end of the experiment minus the number of cells seeded at the beginning of the experiment. The results of this experiment demonstrate that the anti-hPG MAb3 is effective to reduce the growth of Capan 1 metastatic pancreatic cancer cells in vitro, compared to a control antibody.

8.10 Example 10: Inhibitory Effect of 2D Treatment with Anti-hPG Monoclonal Antibodies on Growth of BxPC-3 Cells This example demonstrates the inhibitory effect of anti-hPG monoclonal antibodies on the growth of BxPC-3 primary pancreatic cancer cells in culture.

8.10.1 Method

For each experiment, 150 000 BxPC-3 cells were seeded into 6-well plates and grown in medium containing 10% fetal calf serum for 8 hours. Cells were serum-starved overnight, and starting at 24 hours after seeding (time T0), cells were treated every 12 hours for 48 hours, in the presence of 0.5% PanexinH, with 1 μg/ml of control monoclonal antibody (P3X63Ag8, ATCC, Ref TIB-9) or with 1 μg/ml anti-hPG MAb8 as indicated.

The number of live cells in both control MAb and anti-hPG MAb treated cells was counted at 48 hours. Cell counts at the start of the treatment (T0) were subtracted from test and control cell counts measured at 48 hours.

8.10.2 Results

Results are shown in FIG. 8. Actual cell numbers for both control and test sample, and cell numbers of test sample relative to control, are provided in TABLE 4, below:

TABLE 4

| BxPC-3(T0 = 129 944) | Cell Numbers - T0 | % of Control |
|---|---|---|
| CT MAb | 125 056 +/− 13294 | |
| Anti-hPG MAb8 | 66 056 +/− 16 971 | 53% |

8.11 Example 11: Inhibitory Effect of 2D Treatment with Anti-hPG Monoclonal Antibodies on Growth of MIA PaCa-2 Cells This example demonstrates the inhibitory effect of anti-hPG monoclonal antibodies on the growth of MIA PaCa-2 primary pancreatic cancer cells in culture 8.11.1 Method For each experiment, 100 000 MIA PaCa-2 cells were seeded into 6-well plates and grown in medium containing 10% fetal calf serum +2.5% horse serum for 8 hours. Cells were serum-starved overnight, and starting at 24 hours after seeding (time T0), cells were treated every 12 hours for 72 hours, in the presence of 0.5% Panexin H, with 10 μg/ml of control monoclonal antibody (P3X63Ag8, ATCC, Ref TIB-9) or with 10 μg/ml of anti-hPG MAb8 as indicated. The number of live cells in both control MAb and anti-hPG MAb treated cells was counted at 72 hours. Cell counts at the start of the treatment (T0) were subtracted from test and control cell counts measured at 72 hours.

8.11.2 Results

The results of the experiment are provided in FIG. 9. Actual cell numbers for both control and test sample, and cell numbers of test sample relative to control, are provided in TABLE 5, below:

TABLE 5

| MIA PaCa-2 (T0 = 96 333) | Cell Numbers - T0 | % of Control |
|---|---|---|
| CT MAb | 264 900 +/− 11 927 | |
| Anti-hPG MAb 8 | 181 167 +/− 236 | 68% |

8.12 Example 12: Inhibitory Effect of 2D Pre-Treatment with an Anti-Progastrin Monoclonal Antibody on the Subsequent Growth of Pancreatic Cancer Cells as Cancer Spheres in Suspension This example demonstrates the inhibitory effect that pre-treatment of metastatic pancreatic cancer cells with an anti-progastrin monoclonal antibody has on the subsequent capacity of these cells to grow as cancer spheres under low adherence culture conditions

8.12.1 Experiment 1: Method 100,000 Capan 1 cells/well were first seeded into 6-well plates in DMEM with 20% FCS, serum starved overnight and grown for 48 hours in DMEM with 0.5% Panexin H, in the presence of anti-progastrin monoclonal antibody MAb3 or control monoclonal antibody (mouse anti-human IgG1; Calbiochem ref #411451). At the end of treatment, for each treatment group, 500 cells/well were plated into eight wells of ultra low-adherence 24-well plates in 500 µl of serum-free M11 medium containing bFGF and EGF, and grown for a further 11 days without treatment. At the end of this period, photographs were taken, the number of spheres per well was counted, and sphere surface was measured.

8.12.2 Experiment 1: Results

Photos were taken at the end of the 11-day "washout" period, during which Capan 1 cells from all original treatment conditions were grown in the same M11 medium. Thereafter, an operator who was blinded to the identity of all wells counted the spheres.

As shown in FIG. 10, the ability of Capan 1 pancreatic cancer cells to grow as spheroids in low-adherence plates was significantly reduced by the prior 48-hour treatment with a monoclonal antibody against progastrin.

8.12.3 Experiment 2: Method 150,000 cells/well (metastatic pancreatic cancer cell line SU.86.86) were first seeded into 6-well plates (conventional adherent culture-ware) for 8 hours in RPMI with 10% FCS, serum starved overnight and grown for 48 hours in RPMI with 0.5% Panexin H, in the absence or the presence of anti-progastrin monoclonal antibody MAb8, MAb13, MAb16, or MAb19. At the end of treatment, for each treatment group, 50 cells/well were plated into eight wells of ultra low-adherence 96-well plates in 100 µl of serum-free M11 medium containing bFGF and EGF, and grown for a further 6 days without treatment. At the end of this period, photographs were taken, the number of spheres per well was counted, and sphere surface was measured.

8.12.4 Experiment 2: Results

Photos were taken at the end of the 6-day "washout" period, during which SU.86.86 cells from all original treatment conditions were grown in the same M11 medium. Thereafter, an operator who was blinded to the identity of all wells counted the spheres.

As shown FIG. 11, the ability of SU.86.86 pancreatic cancer cells to grow as spheroids in low-adherence plates was significantly reduced by the prior 48-hour treatment with a monoclonal antibody against progastrin.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

---

What is claimed is:

1. A method for treating pancreatic cancer in a subject, comprising administering to a human subject diagnosed with pancreatic cancer an amount of an anti-human progastrin (anti-hPG) antibody sufficient to provide therapeutic benefit, wherein said anti-hPG antibody is a C-terminal monoclonal antibody that binds to a C-terminal region of human progastrin polypeptide (hPG) wherein the anti-hPG antibody comprises:
   (i) a heavy chain variable region in which CDR1 comprises the amino acid sequence of VH CDR 1.8 (SEQ ID NO:37), CDR2 comprises the amino acid sequence of VH CDR 2.8 (SEQ ID NO:41), and CDR3 comprises the amino acid sequence of VH CDR 3.8 MO ID NO:45), and a light chain variable region in which CDR1 comprises the amino acid sequence of VL CDR 1.8 (SEQ ID NO:49), CDR2 comprises the amino acid sequence of VL CDR 2.8 (SEQ ID NO:52), and CDR3 comprises the amino acid sequence of VL CDR 3.8 (SEQ ID NO:55); or
   (ii) a heavy chain variable region in which CDR1 comprises the amino acid sequence of VH CDR 1.13 (SEQ ID NO:38), CDR2 comprises the amino acid sequence of VH CDR 2.13 (SEQ ID NO:42), and CDR3 comprises the amino acid sequence of VH CDR 3.13 (SEQ ID NO:46), and a light chain variable region in which CDR1 comprises the amino acid sequence of VL CDR 1.13 (SEQ ID NO:50), CDR2 comprises the amino acid sequence of VL CDR 2.13 (SEQ ID NO:53), and CDR3 comprises the amino acid sequence of VL CDR 3.13 (SEQ ID NO:56).

2. The method of claim 1 in which the anti-hPG antibody is humanized.

3. The method of claim 1 in which the C-terminal anti-hPG monoclonal antibody competes for binding hPG with a reference antibody selected from:
   (a) a monoclonal antibody comprising a heavy chain variable domain sequence of SEQ ID NO:59 and a light chain variable domain sequence of SEQ ID NO:63; and
   (b) a monoclonal antibody comprising a heavy chain variable domain sequence of SEQ ID NO:60 and a light chain variable domain sequence of SEQ ID NO:64.

4. The method of claim 1 in which the pancreatic cancer is primary pancreatic cancer.

5. The method of claim 1 in which the pancreatic cancer is metastatic pancreatic cancer.

6. The method of claim 1 in which the anti-hPG monoclonal antibody is administered adjunctive to surgical resection of the tumor.

7. The method of claim 1 in which the anti-hPG monoclonal antibody is administered adjunctive to chemotherapy.

8. A method of inhibiting proliferation of a pancreatic tumor cell comprising exposing the cell to an amount of an anti-human progastrin (anti-hPG) antibody sufficient to inhibit its proliferation, wherein said anti-hPG antibody is a C-terminal monoclonal antibody that binds to a C-terminal region of human progastrin polypeptide,
   wherein the anti-hPG antibody comprises:
   (i) a heavy chain variable region in which CDR1 comprises the amino acid sequence of VH CDR 1.8 (SEQ ID NO:37), CDR2 comprises the amino acid sequence of VH CDR 2.8 (SEQ ID NO:41), and CDR3 comprises the amino acid sequence of VH CDR 3.8 (SEQ ID NO:45), and a light chain variable region in which CDR1 comprises the amino acid sequence of VL CDR 1.8 (SEQ ID NO:49), CDR2 comprises the amino acid sequence of VL CDR 2.8 (SEQ ID NO:52), and CDR3 comprises the amino acid sequence of VL CDR 3.8 (SEQ ID NO:55); or (ii) a heavy chain variable region in which CDR1 comprises the amino acid sequence of VH CDR 1.13 (SEQ ID NO:38), CDR2 comprises the amino acid sequence of VH CDR 2.13 (SEQ ID NO:42), and CDR3 comprises the amino acid sequence of VH CDR 3.13 (SEQ ID NO:46), and a light chain variable region in which CDR1 comprises the amino acid sequence of VL CDR 1.13 (SEQ ID NO:50), CDR2 comprises the amino acid sequence of VL CDR 2.13 (SEQ ID NO:53), and CDR3 comprises the amino acid sequence of VL CDR 3.13 (SEQ ID NO:56).

9. The method of claim 8 in which is practiced in vitro.

10. The method of claim 8 which is practiced in vivo.

* * * * *

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 13
<211> LENGTH: 112
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
    50                  55                  60

Lys Gly Lys Ala Thr Phe Thr Ala Asp Thr Ser Ser Asp Thr Ala Tyr
65                  70                  75                  80

Met Leu Leu Ser Ser Leu Thr Ser Glu Asp Ser Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30
```

```
Ser Gly Val Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
            100                 105                 110
```

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(345)

<400> SEQUENCE: 16

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
            100                 105                 110 gtc tcc tca                                                       345
Val Ser Ser
        115
```

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15
```

```
gat caa gcc tcc atc tct tgc aga tct agt cag agc att gta cat agt        96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct       144
Asn Gly Asn Thr Tyr Leu Glu Trp Tyr Leu Gln Lys Pro Gly Gln Ser
35                  40                  45 cca aag ctc ctg atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc       240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt       288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa       336
Ser His Val Pro Phe Thr Phe Gly Gly Gly Thr Lys Leu Glu Ile Lys
            100                 105                 110

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 18 cag gtt cag ttg cag cag tct gga gct gag ctg atg aag cca ggg gcc        48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc        96
Ser Val Lys Ile Ser Cys Lys Ala Thr Gly Tyr Thr Phe Ser Ser Ser
            20                  25                  30 tgg ata gag tgg tta aaa cag agg cct gga cat ggc ctt gag tgg att       144
Trp Ile Glu Trp Leu Lys Gln Arg Pro Gly His Gly Leu Glu Trp Ile
        35                  40                  45 gga gag ttt tta cct gga agt ggt agt aca gac tac aat gag aag ttc       192
Gly Glu Phe Leu Pro Gly Ser Gly Ser Thr Asp Tyr Asn Glu Lys Phe
    50                  55                  60 aag ggc aag gcc aca ttc act gca gac aca tcc tcc gac aca gcc tac       240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt       288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act       336
Ala Thr Asp Gly Asn Tyr Asp Trp Phe Ala Tyr Trp Gly Gln Gly Thr
            100                 105                 110 ctg gtc act gtc tct gca                                               354
Leu Val Thr Val Ser Ala
        115

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: CDS
<222> LOCATION: (1)..(336)

<400> SEQUENCE: 19 gat ctt gtg atg acc caa act cca ctc tcc ctg cct gtc agt ctt gga      48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt      96
Asp Gln Ala Ser Ile Ser Cys Arg Ser Ser Gln Ser Leu Val His Ser
            20                  25                  30 agt gga gtc acc tat tta cat tgg tac ctg cag aag cca ggc cag tct     144
Ser Gly Val Thr Tyr Leu His Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt     288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa     336
Thr His Val Pro Pro Thr Phe Gly Ser Gly Thr Lys Leu Glu Ile Lys
            100                 105                 110

<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
        35                  40                  45

Gly Gly Phe Tyr Pro Gly Asn Ser Asp Ser Arg Tyr Ser Gln Lys Phe
    50                  55                  60
```

```
Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Arg Asp Ser Pro Gln Tyr Trp Gly Gln Gly Thr Leu Val Thr
            100                 105                 110

Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Phe Thr Phe Gly Gly Gly Thr Lys Val Glu Ile Lys
            100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ser Ser Ser
                 20                  25                  30

Trp Met His Trp Val Arg Gln Ala Pro Gly Gln Gly Leu Glu Trp Met
            35                  40                  45

Gly Ile Phe Leu Pro Gly Ser Gly Ser Thr Asp Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ser
            115
```

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15

<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 28
<211> LENGTH: 5

```
<212> TYPE: PRT
<213> ORGANISM: Homo sapiens

<400> SEQUENCE: 28

Asp Ala Pro Leu Gly
1               5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
1

<210> SEQ ID NO 34
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens
```

```
<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Thr Gln Gly Asn Tyr Ser Leu Asp Phe
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5
```

```
<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Gly Gly Tyr Tyr Pro Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Glu Val Asn Tyr Gly Asp Ser Tyr His Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Arg His Thr Lys Gly Ile Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Leu Leu Asp Ser Asp Gly Lys Thr Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gln Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Ser Glu Asp Thr Ala Ile Tyr Tyr Cys
                85                  90                  95

Ala Arg Gly Thr Gly Thr Tyr Trp Gly Gln Gly Thr Thr Leu Thr Val
            100                 105                 110

Ser Ser
```

```
<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Tyr Tyr Pro Phe Asp Tyr Trp Gly Gln Gly Thr Thr
            100                 105                 110

Leu Thr Val Ser Ser
        115

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63
```

```
Asp Ile Val Met Thr Gln Ala Ala Ser Ser Asn Pro Val Thr Leu Gly
1               5                   10                  15

Thr Ser Ala Ser Ile Ser Cys Arg Ser Ser Lys Ser Leu Arg His Thr
            20                  25                  30

Lys Gly Ile Thr Phe Leu Tyr Trp Tyr Leu Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Leu Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 64

```
Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 65

```
Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ala Ser Phe Ser Leu Gly Ala
1               5                   10                  15

Ser Ala Lys Leu Thr Cys Thr Leu Ser Ser Gln His Arg Thr Tyr Thr
                20                  25                  30

Ile Glu Trp Tyr Gln Gln Ser Leu Lys Pro Pro Lys Tyr Val Met
            35                  40                  45

Glu Val Lys Lys Asp Gly Ser His Ser Thr Gly His Gly Ile Pro Asp
50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat      96
Ser Leu Lys Leu Ser Cys Ala Ala Ser Gly Phe Thr Phe Thr Thr Tyr
                20                  25                  30 gcc atg tct tgg gtt cgc cag act ccg gag aag agg ctg gag tgg gtc     144
Ala Met Ser Trp Val Arg Gln Thr Pro Glu Lys Arg Leu Glu Trp Val
            35                  40                  45 gca acc att agt agt ggt ggt act tac acc tac tat cca gac agt gtg     192
Ala Thr Ile Ser Ser Gly Gly Thr Tyr Thr Tyr Tyr Pro Asp Ser Val
50                  55                  60 aag ggt cga ttc acc atc tcc aga gac aat gcc aag aac gcc cta tac     240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt     288
Leu Gln Met Ser Ser Leu Arg Ser Glu Asp Thr Ala Met Tyr Tyr Cys
                85                  90                  95
```

```
gca aca cag ggg aat tac tct ttg gac ttc tgg ggc caa ggc acc tct      336
Ala Thr Gln Gly Asn Tyr Ser Leu Asp Phe Trp Gly Gln Gly Thr Ser
            100                 105                 110 ctc aca gtc tcc tca                                                   351
Leu Thr Val Ser Ser
        115

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68 gag gtg cag ctg gtg gag tct ggg gga ggc ttg gtg cag cct gga ggg       48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat       96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc      144
Gly Met Ser Trp Val Arg Gln Ser Pro Asp Arg Arg Leu Glu Leu Val
        35                  40                  45 gca agt att aat act ttt ggt gat aga acc tat tat cca gac agt gtg      192
Ala Ser Ile Asn Thr Phe Gly Asp Arg Thr Tyr Tyr Pro Asp Ser Val
    50                  55                  60 aag ggc cga ttc acc atc tcc aga gac aat gcc aag aac acc ctg tac      240
Lys Gly Arg Phe Thr Ile Ser Arg Asp Asn Ala Lys Asn Thr Leu Tyr
65                  70                  75                  80 ctg caa atg acc agt ctg aag tct gag gac aca gcc att tat tac tgt      288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc      336
Ala Arg Gly Thr Gly Thr Tyr Trp Gly Gln Gly Thr Thr Leu Thr Val
            100                 105                 110 tcc tca                                                               342
Ser Ser <210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 69 cag gtc caa ctg cag cag tct ggg gct gaa ctg gtg aag cct ggg gct       48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac       96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att      144
Tyr Met Tyr Trp Val Lys Gln Arg Pro Gly Gln Gly Leu Glu Trp Ile
        35                  40                  45
```

```
gga gag att aat cct agc aat ggt ggt act aac ttc aat gag aag ttc      192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac      240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt      288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act      336
Thr Arg Gly Gly Tyr Tyr Pro Phe Asp Tyr Trp Gly Gln Gly Thr Thr
                100                 105                 110 ctc aca gtc tcc tca                                                  351
Leu Thr Val Ser Ser
        115

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70 gat gtg cag ctt cag gag tcg gga cct ggc ctg gtg aaa cct tct cag      48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat      96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg      144
Tyr Ala Trp Asn Trp Ile Arg Gln Phe Pro Gly Asn Lys Leu Glu Trp
            35                  40                  45 atg ggc tac ata agc ttc agt ggt tac act agt tac aac cca tct ctc      192
Met Gly Tyr Ile Ser Phe Ser Gly Tyr Thr Ser Tyr Asn Pro Ser Leu
        50                  55                  60 aaa agt cga atc tct gtc act cgg gac aca tcc agg aac caa ttc ttc      240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt      288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc      336
Ala Arg Glu Val Asn Tyr Gly Asp Ser Tyr His Phe Asp Tyr Trp Gly
                100                 105                 110 caa ggc acc att gtc aca gtc tcc tca                                  363
Gln Gly Thr Ile Val Thr Val Ser Ser
        115                 120

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)
```

```
<400> SEQUENCE: 71 gac att gtg atg acg cag gct gca tcc tct aat cca gtc act ctt gga     48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act     96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct    144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca    192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc    240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat    288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa    336
Leu Glu Leu Pro Leu Thr Phe Gly Ala Gly Thr Lys Leu Glu Leu Lys
            100                 105                 110

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 72 gat gtt gtg ctg acc cag act cca ctc act ttg tcg gtt acc att gga     48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt     96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct    144
Asp Gly Lys Thr Tyr Leu Asn Trp Leu Leu Gln Arg Pro Gly Gln Ser
        35                  40                  45 cca aag cgc cta atc tat ctg gtg tct aaa ctg gac tct gga gtc cct    192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aaa atc    240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt    288
Ser Arg Val Glu Ala Glu Asp Leu Gly Val Tyr Tyr Cys Trp Gln Gly
                85                  90                  95 aca cat ttt cct cag acg ttc ggt gga ggc acc aag ctg gaa atc aaa    336
Thr His Phe Pro Gln Thr Phe Gly Gly Gly Thr Lys Leu Glu Ile Lys
            100                 105                 110

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic
```

-continued

```
<220> FEATURE:
<221> NAME/KEY: CDS
<222> LOCATION: (1)..(336)

<400> SEQUENCE: 73 gat gtt gtg atg acc cag act cca ctc act ttg tcg gtt acc att ggg      48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt      96
Arg Pro Ala Ser Ile Ser Cys Lys Ser Ser Gln Ser Leu Leu Asp Ser
            20                  25                  30 gat gga aag aca tat ttg tat tgg ttg tta cag agg cca ggc cag tct     144
Asp Gly Lys Thr Tyr Leu Tyr Trp Leu Leu Gln Arg Pro Gly Gln Ser
        35                  40                  45 cca aag cgc cta atc tat ctg gtg tct gag ctg gac tct gga gtc cct     192
Pro Lys Arg Leu Ile Tyr Leu Val Ser Glu Leu Asp Ser Gly Val Pro
    50                  55                  60 gac agg atc act ggc agt ggg tcg ggg aca gat ttc aca ctg aag atc     240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga     288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa     336
Thr His Ser Pro Tyr Thr Phe Gly Gly Gly Thr Lys Leu Glu Ile Lys
            100                 105                 110

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74 caa ctt gcg ctc act cag tca tct tca gcc tct ttc tcc ctg gga gcc      48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc      96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg     144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat     192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc     240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat     288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc     336
Ala Ile Lys Gly Gln Ser Val Phe Val Phe Gly Gly Gly Thr Lys Val
            100                 105                 110 act gtc cta                                                         345
Thr Val Leu
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
            115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
50                  55                  60
```

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Thr Gln Gly Asn Tyr Ser Leu Asp Phe Trp Gly Gly Gly Thr Thr
         100                 105                 110

Val Thr Val Ser Ser
        115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Gly Thr Gly Thr Tyr Trp Gly Gln Gly Thr Leu Val Thr Val
         100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
             85                  90                  95

Thr His Phe Pro Gln Thr Phe Gly Gly Gly Thr Lys Val Glu Ile Lys
         100                 105                 110

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
50                  55                  60

Gln Gly Arg Val Thr Met Thr Arg Asp Thr Ser Thr Ser Thr Val Tyr
65                  70                  75                  80

-continued

```
Met Glu Leu Ser Ser Leu Arg Ser Glu Asp Thr Ala Val Tyr Tyr Cys
                 85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 89
```

-continued

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Leu Val Leu Thr Gln Ser Pro Ser Ala Ser Ala Ser Leu Gly Ala
1               5                   10                  15
```

```
Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
65              70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
 50                  55                  60

Lys Ser Arg Val Thr Ile Ser Val Asp Thr Ser Lys Asn Gln Phe Ser
65              70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
 50                  55                  60
```

```
Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
            100                 105                 110

Glu Ile Lys
        115

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Gln
  1               5                  10                  15

Thr Leu Ser Leu Thr Cys Thr Val Ser Gly Tyr Ser Ile Thr Ser Asp
                20                  25                  30

Tyr Ala Trp Asn Trp Ile Arg Gln His Pro Gly Lys Gly Leu Glu Trp
             35                  40                  45

Ile Gly Tyr Ile Ser Phe Ser Gly Tyr Thr Ser Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
             35                  40                  45

Glu Val Lys Lys Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
            100                 105                 110
```

Glu Ile Lys
        115

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

Cys Xaa Xaa Gln Gly Pro Trp Leu Glu Glu Glu Glu Glu Ala Tyr Gly
1               5                   10                  15

Trp Met Asp Phe Gly Arg Arg Ser Ala Glu Asp Glu Asn
            20                  25

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                   10                  15

<210> SEQ ID NO 100
<211> LENGTH: 101
<212> TYPE: PRT
<213> ORGANISM: Homo sapiens

```
<400> SEQUENCE: 100

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
            35                  40                  45

Gln Gln Gly Pro Ala Ser His His Arg Arg Gln Leu Gly Pro Gln Gly
        50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
            35                  40                  45

Ala Asp Pro Ser Lys Lys Gln Gly Pro Trp Leu Glu Glu Glu Glu Glu
        50                  55                  60

Ala Tyr Gly Trp Met Asp Phe Gly Arg Arg Ser Ala Glu Asp Glu Asn
65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30

Asp Phe

<210> SEQ ID NO 103
<211> LENGTH: 35
<212> TYPE: PRT
<213> ORGANISM: Homo Sapiens

<400> SEQUENCE: 103

Gln Leu Gly Pro Gln Gly Pro Pro His Leu Val Ala Asp Pro Ser Lys
1               5                   10                  15

Lys Gln Gly Pro Trp Leu Glu Glu Glu Glu Glu Ala Tyr Gly Trp Met
            20                  25                  30

Asp Phe Gly
        35
```

```
<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Ala Tyr Gly Trp Met Asp
1               5                   10                  15

Phe

<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15

Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```